US012806126B2

(12) United States Patent
Agach et al.

(10) Patent No.: US 12,806,126 B2
(45) Date of Patent: Nov. 24, 2026

(54) COMPOSITION COMPRISING N,N-DICARBOXYMETHYLGLUTAMIC ACID, 1,3-PROPANEDIOL, AT LEAST ONE NONIONIC SURFACTANT, AT LEAST ONE ALKALINE AGENT AND/OR AT LEAST ONE DYE

(71) Applicant: L'Oreal, Paris (FR)

(72) Inventors: Mickaël Agach, Saint Ouen (FR); Sarah Boulemnakher, Saint Ouen (FR); Hanène Moueddene, Saint Ouen (FR); Marie Giafferi, Saint Ouen (FR); Julie Bruyere, Saint Ouen (FR)

(73) Assignee: L'Oreal, Paris (FR)

( * ) Notice: Subject to any disclaimer, the term of this patent is extended or adjusted under 35 U.S.C. 154(b) by 319 days.

(21) Appl. No.: 18/573,917

(22) PCT Filed: Jun. 29, 2022

(86) PCT No.: PCT/EP2022/068001
§ 371 (c)(1),
(2) Date: Dec. 22, 2023

(87) PCT Pub. No.: WO2023/275209
PCT Pub. Date: Jan. 5, 2023

(65) Prior Publication Data

US 2024/0285495 A1 Aug. 29, 2024

(30) Foreign Application Priority Data

Jun. 30, 2021 (FR) ....................................... 2107103

(51) Int. Cl.

| | |
|---|---|
| ***A61K 8/44*** | (2006.01) |
| ***A61K 8/22*** | (2006.01) |
| ***A61K 8/34*** | (2006.01) |
| ***A61Q 5/06*** | (2006.01) |
| ***A61Q 5/08*** | (2006.01) |

(52) U.S. Cl.
CPC .................. *A61K 8/44* (2013.01); *A61K 8/22* (2013.01); *A61K 8/345* (2013.01); *A61Q 5/065* (2013.01); *A61Q 5/08* (2013.01); *A61K 2800/43* (2013.01); *A61K 2800/4322* (2013.01)

(58) Field of Classification Search
CPC ............ A61K 8/44; A61K 8/22; A61K 8/345; A61K 2800/43; A61K 2800/4322; A61K 2800/882; A61K 8/41; A61K 8/604; A61Q 5/065; A61Q 5/08; A61Q 5/10
See application file for complete search history.

(56) References Cited

U.S. PATENT DOCUMENTS

2018/0326228 A1 11/2018 Nocker et al.
2021/0128426 A1 5/2021 Lanzi

FOREIGN PATENT DOCUMENTS

FR 3086172 A1 3/2020
FR 3098115 A1 1/2021
IT 201900005622 A1 10/2020

OTHER PUBLICATIONS

International Search Report and Written Opinion mailed Oct. 5, 2022, issued in corresponding International Application No. PCT/EP2022/068001, filed Jun. 29, 2022, 17 pages.
Grevalcuore, K., et al., "Hair Care Composition," Research Disclosure, Apr. 2020, 4 pages.
"Real Coffee Hair Color Cream," Door Cosmetics, South Korea, Jan. 2019 <http://www.gnpd.com>, 2 pages.

*Primary Examiner* — Robert A Wax
*Assistant Examiner* — Quanglong N Truong
(74) *Attorney, Agent, or Firm* — CHRISTENSEN O'CONNOR JOHNSON KINDNESS PLLC

(57) ABSTRACT

The present invention relates to a cosmetic composition for treating keratin fibres, notably human keratin fibres such as the hair, comprising N,N-dicarboxymethylglutamic acid, and/or salts thereof, solvates thereof and/or solvates of the salts thereof, 1,3-propanediol, at least one nonionic-surfactant chosen from ($C_6$-$C_{24}$ alkyl)polyglycosides, esters of $C_8$-$C_{30}$ fatty acids and of (poly)oxyalkylenated glycerol ethers, in particular of oxyethylenated and/or oxypropylenated glycerol ethers, and mixtures thereof, at least one alkaline agent and/or at least one dye. The present invention also relates to a process for dyeing and/or lightening keratin fibres, such as the hair, in which a composition comprising N,N-dicarboxymethylglutamic acid, and/or salts thereof, solvates thereof and/or solvates of the salts thereof, 1,3-propanediol, at least one nonionic surfactant, at least one alkaline agent and/or at least one dye is applied to said fibres. The present invention also relates to the use of the composition according to the invention for dyeing and/or lightening keratin fibres such as the hair.

15 Claims, No Drawings

COMPOSITION COMPRISING N,N-DICARBOXYMETHYLGLUTAMIC ACID, 1,3-PROPANEDIOL, AT LEAST ONE NONIONIC SURFACTANT, AT LEAST ONE ALKALINE AGENT AND/OR AT LEAST ONE DYE

The present invention relates to a cosmetic composition for treating keratin fibres, notably human keratin fibres such as the hair, comprising N,N-dicarboxymethylglutamic acid, a salt thereof, solvates thereof and/or solvates of the salts thereof, 1,3-propanediol in a content as defined below, at least one nonionic surfactant, at least one alkaline agent and/or at least one dye.

The present invention also relates to a process for dyeing and/or lightening keratin fibres, such as the hair, in which the composition as described previously is applied to said fibres.

In particular, the present invention also relates to a process for dyeing keratin fibres, such as the hair, in which the composition as described previously, and comprising at least one dye, preferably chosen from oxidation dyes, direct dyes and mixtures thereof, is applied to said fibres.

The present invention also relates to the use of the composition according to the invention for dyeing and/or lightening, preferably for dyeing keratin fibres such as the hair.

In processes for dyeing keratin fibres, it is known practice to dye keratin fibres via various techniques using direct dyes for non-permanent dyeing, or oxidation dye precursors for permanent dyeing.

Non-permanent dyeing or direct dyeing consists in dyeing keratin fibres with dye compositions containing direct dyes. These dyes are coloured and colouring molecules that have affinity for keratin fibres. They are applied to the keratin fibres for a time necessary to obtain the desired colouring, and are then rinsed out.

Some of these dyes may be used under lightening conditions, which enables the production of colourings that are visible on dark hair.

It is also known practice to dye keratin fibres permanently via oxidation dyeing. This dyeing technique consists in applying to the keratin fibres a composition containing dye precursors such as oxidation bases and couplers. Under the action of an oxidizing agent, these precursors form one or more coloured substances in the hair.

The existing dyeing and/or lightening processes generally use cosmetic compositions comprising a certain number of ingredients for which the regulatory conditions are increasingly stringent. It is thus necessary to develop compositions comprising alternative ingredients.

Consumers are notably in search of dyeing and/or lightening products that are more environmentally friendly, notably based on ingredients of natural origin, and which have good working qualities, are easy to use and give good dyeing and/or lightening properties.

Furthermore, the "natural" dye compositions that are currently available on the market do not make it possible to obtain colourings that are sufficiently persistent with respect to external agents such as light, perspiration, washing, or even rubbing.

The performance of the colourings obtained with such compositions is also poorer compared with the performance obtained with conventional dye compositions, notably in terms of colour build-up, strength and chromaticity.

Moreover, such compositions are not entirely satisfactory in terms of the cosmetic properties of the hair either.

Thus, there is a real need for a composition for dyeing and/or lightening keratin fibres, in particular human keratin fibres such as the hair, which is more environmentally friendly and which does not have the abovementioned drawbacks, i.e. which is capable of giving good performance, notably in terms of colour build-up, strength and chromaticity, when it comprises one or more dyes, and/or good lightening performance while at the same time having low selectivity and good persistence and which is capable of giving good dyeing performance, and/or good lightening performance, even after a period of storage, while at the same time having good working qualities.

One subject of the present invention is thus a composition comprising:

- one or more compounds chosen from N,N-dicarboxymethylglutamic acid, salts thereof, solvates thereof, solvates of the salts thereof and mixtures thereof,
- 1,3-propanediol in a content of greater than or equal to 3% by weight relative to the total weight of the composition,
- one or more nonionic surfactants chosen from ($C_6$-$C_{24}$ alkyl)polyglycosides, esters of $C_8$-$C_{30}$ fatty acids and of (poly)oxyalkylenated glycerol ethers, in particular of oxyethylenated and/or oxypropylenated glycerol ethers, and mixtures thereof,
- one or more alkaline agents and/or one or more dyes.

The composition according to the invention makes it possible to achieve the above objectives, notably in terms of colour build-up, dyeing power, chromaticity, selectivity, persistence of the colouring, in particular with respect to shampoos when it comprises one or more dyes, and/or good performance in terms of lightening, and also good working qualities.

The composition according to the invention also makes it possible to lead to good cosmeticity, notably in terms of sheen, a more natural feel, and a good level of comfort, while at the same time preserving the integrity of the fibre.

The composition according to the invention also has the advantage of leading to efficient lightening of keratin fibres while at the same time reducing the unpleasant and aggressive odours, notably of ammonia, which are liable to be given off when it is applied to said fibres.

Moreover, the composition according to the invention shows good stability, notably on storage. The composition may notably comprise dyes and/or other compounds in salt form.

Moreover, the composition according to the invention has good working qualities, notably a creamy texture allowing quick and easy mixing with an oxidizing composition, where appropriate, and easy and uniform spreading over the entire head of hair. The composition according to the invention has good stability over time, notably little or no change in its viscosity during storage.

The present invention also relates to a process for dyeing and/or lightening keratin fibres, in particular human keratin fibres such as the hair, in which a composition is applied to said fibres, comprising:

- one or more compounds chosen from N,N-dicarboxymethylglutamic acid, salts thereof, solvates thereof, solvates of the salts thereof and mixtures thereof,
- 1,3-propanediol in a content of greater than or equal to 3% by weight relative to the total weight of the composition,
- one or more nonionic surfactants chosen from ($C_6$-$C_{24}$ alkyl)polyglycosides, esters of $C_8$-$C_{30}$ fatty acids and of (poly)oxyalkylenated glycerol ethers, in particular of oxyethylenated and/or oxypropylenated glycerol ethers, and mixtures thereof, one or more dyes, and/or one or more alkaline agents.

The present invention also relates to a process for dyeing keratin fibres, in particular human keratin fibres such as the hair, in which a composition is applied to said fibres, comprising:

one or more compounds chosen from N,N-dicarboxymethylglutamic acid, salts thereof, solvates thereof, solvates of the salts thereof and mixtures thereof, 1,3-propanediol in a content of greater than or equal to 3% by weight relative to the total weight of the composition, one or more nonionic surfactants chosen from ($C_6$-$C_{24}$ alkyl)polyglycosides, esters of $C_8$-$C_{30}$ fatty acids and of (poly)oxyalkylenated glycerol ethers, in particular of oxyethylenated and/or oxypropylenated glycerol ethers, and mixtures thereof, one or more dyes, and optionally one or more alkaline agents.

The present invention also relates to the use of the composition according to the invention for dyeing and/or lightening keratin fibres, preferably dyeing keratin fibres, in particular human keratin fibres such as the hair.

Other subjects, characteristics, aspects and advantages of the invention will emerge even more clearly on reading the description and the example that follows.

In the text hereinbelow, unless otherwise indicated, the limits of a range of values are included in that range, notably in the expressions "between" and "ranging from . . . to . . . ".

Moreover, the expression "at least one" used in the present description is equivalent to the expression "one or more".

N,N-Dicarboxymethylglutamic acid, Salts Thereof

The composition according to the invention comprises one or more compounds chosen from N,N-dicarboxymethylglutamic acid, salts thereof, solvates thereof, solvates of the salts thereof and mixtures thereof.

The salts are notably alkali metal, alkaline-earth metal, ammonium and substituted ammonium salts.

Among the salts of these compounds, the alkali metal salts and notably the sodium or potassium salts are preferred.

The composition according to the invention preferably comprises tetrasodium glutamate diacetate (GLDA). Use will be made, for example, of Dissolvine GL38 or 45S from AkzoNobel.

Preferably, the total content of compound(s) chosen from N,N-dicarboxymethylglutamic acid, salts thereof, solvates thereof, solvates of the salts thereof and mixtures thereof ranges from 0.001% to 15% by weight, more preferentially from 0.005% to 10% by weight, better still from 0.01% to 8% by weight, even better still from 0.05% to 5% by weight, or even from 0.075% to 2% by weight, or even from 0.1% to 1% by weight, relative to the total weight of the composition.

According to a preferred embodiment, the total content of tetrasodium glutamate diacetate (GLDA) ranges from 0.001% to 15% by weight, more preferentially from 0.005% to 10% by weight, better still from 0.01% to 8% by weight, even better still from 0.05% to 5% by weight, or even from 0.075% to 2% by weight, or even from 0.1% to 1% by weight, relative to the total weight of the composition.

1,3-Propanediol

The composition according to the invention also comprises 1,3-propanediol.

The content of 1,3-propanediol is greater than or equal to 3% by weight, preferably ranging from 3% to 15% by weight, more preferentially from 4% to 10% by weight, more preferentially from 4% to 7% by weight relative to the total weight of the composition.

Nonionic Surfactants

The composition according to the present invention also comprises one or more nonionic surfactants chosen from ($C_6$-$C_{24}$ alkyl)polyglycosides, esters of $C_8$-$C_{30}$ fatty acids and of (poly)oxyalkylenated glycerol ethers, and mixtures thereof.

The nonionic surfactant(s) that may be used in the composition of the present invention are notably described, for example, in the "Handbook of Surfactants" by M. R. Porter, published by Blackie & Son (Glasgow and London), 1991, pages 116-178.

The nonionic surfactants are chosen from ($C_6$-$C_{24}$ alkyl) polyglycosides, esters of $C_8$-$C_{30}$ fatty acids and of (poly) oxyalkylenated glycerol ethers, in particular of oxyethylenated and/or oxypropylenated glycerol ethers, and mixtures thereof.

The esters of $C_8$-$C_{30}$, notably $C_8$-$C_{24}$ and preferably $C_{16}$-$C_{22}$ fatty acids and of (poly)oxyalkylenated, in particular oxyethylenated and/or oxypropylenated, glycerol ethers, may include more than 10 oxyethylene and/or oxypropylene units, in particular from 15 to 200 units, better still from 15 to 100 oxyethylene and/or oxypropylene units.

Esters of a $C_8$-$C_{30}$ fatty acid, notably a $C_8$-$C_{24}$ and preferably $C_{16}$-$C_{22}$ fatty acid, and of (poly)oxyalkylenated glycerol ethers, in particular oxyethylenated and/or oxypropylenated glycerol ethers are preferably chosen from polyoxyethylenated glyceryl monostearate containing 200 oxyethylene units, sold under the name Simulsol 220 TM® by the company SEPPIC; polyoxyethylenated glyceryl stearate containing 30 oxyethylene units, for instance the product Tagat S® sold by the company Goldschmidt, polyoxyethylenated glyceryl oleate containing 30 oxyethylene units, for instance the product Tagat O® sold by the company Goldschmidt, polyoxyethylenated glyceryl cocoate containing 30 oxyethylene units, for instance the product Varionic LI 13® sold by the company Sherex, polyoxyethylenated glyceryl isostearate containing 30 oxyethylene units, for instance the product Tagat L® sold by the company Goldschmidt, and polyoxyethylenated glyceryl laurate containing 30 oxyethylene units, for instance the product Tagat I® from the company Goldschmidt.

Preferably, esters of $C_8$-$C_{30}$ fatty acids and of (poly) oxyalkylenated glycerol ethers are chosen from esters of $C_{16}$-$C_{22}$ fatty acids and of oxyethylenated glycerol ethers.

Preferentially, the nonionic surfactants are chosen from ($C_6$-$C_{24}$ alkyl)polyglycosides, such as cocoyl glucoside, caprylyl/capryl glucoside, lauryl glucoside, decyl glucoside and cetearyl glucoside, and mixtures thereof.

Advantageously, the total content of nonionic surfactant(s) chosen from ($C_6$-$C_{24}$ alkyl)polyglycosides preferably ranges from 0.01% to 15% by weight, more preferentially from 0.1% to 10% by weight, better still from 0.2% to 8% by weight, and even better still from 0.3% to 6% by weight relative to the total weight of the composition.

The composition may also contain one or more additional nonionic surfactants different from the nonionic surfactants previously defined, especially different from ($C_6$-$C_{24}$ alkyl) polyglycosides, esters of $C_8$-$C_{30}$ fatty acids and of (poly) oxyalkylenated glycerol ethers, and mixtures thereof.

Examples of such additional nonionic surfactants that may be mentioned include the following compounds, alone or as a mixture:

- oxyalkylenated ($C_8$-$C_{24}$)alkylphenols;
- saturated or unsaturated, linear or branched, oxyalkylenated or glycerolated $C_8$-$C_{40}$ alcohols, preferably including one or two fatty chains;
- saturated or unsaturated, linear or branched, oxyalkylenated $C_8$-$C_{30}$ fatty acid amides;
- esters of saturated or unsaturated, linear or branched, $C_8$-$C_{30}$ fatty acids and of polyethylene glycols;
- oxyethylenated esters of saturated or unsaturated, linear or branched, $C_8$-$C_{30}$ fatty acids and of sorbitol;
- fatty acid esters of sucrose;
- ($C_8$-$C_{30}$)alkenyl(poly)glucosides, which are optionally oxyalkylenated (0 to 10 oxyalkylene units) and comprising from 1 to 15 glucose units, ($C_8$-$C_{30}$)alkyl(poly) glucoside esters;
- saturated or unsaturated oxyethylenated plant oils;
- condensates of ethylene oxide and/or of propylene oxide;
- N—($C_8$-$C_{30}$)alkylglucamine and N—($C_8$-$C_{30}$)acylmethylglucamine derivatives;
- amine oxides.

They are notably chosen from alcohols different from the fatty alcohols used as fatty substances as defined hereafter, α-diols and ($C_1$-$C_{20}$)alkylphenols, these compounds being ethoxylated, propoxylated or glycerolated and containing at least one fatty chain including, for example, from 8 to 18 carbon atoms, the number of ethylene oxide or propylene oxide groups possibly ranging notably from 1 to 200, and the number of glycerol groups possibly ranging notably from 1 to 30.

Mention may also be made of condensates of ethylene oxide and of propylene oxide with fatty alcohols, ethoxylated fatty amides preferably containing from 1 to 30 ethylene oxide units, polyglycerolated fatty amides including on average from 1 to 5, and in particular from 1.5 to 4, glycerol groups, ethoxylated fatty acid esters of sorbitan containing from 1 to 30 ethylene oxide units, fatty acid esters of sucrose, fatty acid esters of polyethylene glycol, ($C_6$-$C_{24}$ alkyl)polyglycosides, oxyethylenated plant oils, N—($C_6$-$C_{24}$ alkyl)glucamine derivatives, amine oxides such as ($C_{10}$-$C_{14}$ alkyl)amine oxides or N—($C_{10}$-$C_{14}$ acyl)aminopropylmorpholine oxides.

The $C_8$-$C_{30}$ and preferably $C_{12}$-$C_{22}$ fatty acid esters (notably monoesters, diesters and triesters) of sorbitan may be chosen from:

sorbitan caprylate; sorbitan cocoate; sorbitan isostearate; sorbitan laurate; sorbitan oleate; sorbitan palmitate; sorbitan stearate; sorbitan diisostearate; sorbitan dioleate; sorbitan distearate; sorbitan sesquicaprylate; sorbitan sesquiisostearate; sorbitan sesquioleate; sorbitan sesquistearate; sorbitan triisostearate; sorbitan trioleate; and sorbitan tristearate.

The polyoxyethylenated $C_8$-$C_{30}$ (preferably $C_{12}$-$C_{18}$) fatty acid esters (notably monoesters, diesters and triesters) of sorbitan notably containing from 2 to 20 mol of ethylene oxide may be chosen from polyoxyethylenated esters of $C_{12}$-$C_{18}$ fatty acids, in particular lauric, myristic, cetylic or stearic acid, of sorbitan notably containing from 2 to 30 mol of ethylene oxide, such as:

- polyoxyethylenated sorbitan monolaurate (4 OE) (Polysorbate-21),
- polyoxyethylenated sorbitan monolaurate (20 OE) (Polysorbate-20),
- polyoxyethylenated sorbitan monopalmitate (20 OE) (Polysorbate-40),
- polyoxyethylenated sorbitan monostearate (20 OE) (Polysorbate-60),
- polyoxyethylenated sorbitan monostearate (4 OE) (Polysorbate-61),
- polyoxyethylenated sorbitan monooleate (20 OE) (Polysorbate-80),
- polyoxyethylenated sorbitan monooleate (5 OE) (Polysorbate-81),
- polyoxyethylenated sorbitan tristearate (20 OE) (Polysorbate-65),
- polyoxyethylenated sorbitan trioleate (20 OE) (Polysorbate-85).

The polyoxyethylenated $C_8$-$C_{30}$ (preferably $C_{12}$-$C_{18}$) fatty acid esters (notably monoesters, diesters, triesters and tetraesters) of sorbitan, notably containing from 2 to 20 mol of ethylene oxide, may be chosen from polyoxyethylenated esters, notably containing from 2 to 20 mol of ethylene oxide, such as of $C_{12}$-$C_{18}$ fatty acids, in particular lauric, myristic, cetylic or stearic acid, and of sorbitan, such as:

- the ester polyoxyethylenated with 20 OE of sorbitan and of cocoic acid (PEG-20 sorbitan cocoate);
- the polyoxyethylenated esters (notably containing from 2 to 20 OE) of sorbitan and of isostearic acid (such as PEG-2 sorbitan isostearate; PEG-5 sorbitan isostearate; PEG-20 sorbitan isostearate such as the product sold under the name Nikkol TI 10 V by the company Nikkol),
- the polyoxyethylenated esters (notably containing from 2 to 20 OE) of sorbitan and of lauric acid (such as PEG-10 sorbitan laurate),
- the polyoxyethylenated esters (notably containing from 2 to 20 OE) of sorbitan and of oleic acid containing 10 oxyethylene groups (such as PEG-6 sorbitan oleate; PEG-20 sorbitan oleate),
- the polyoxyethylenated esters (notably containing from 3 to 20 OE) of sorbitan and of stearic acid (such as PEG-3 sorbitan stearate; PEG-4 sorbitan stearate; PEG-6 sorbitan stearate).

Advantageously, the total content of nonionic surfactant(s) in the composition preferably ranges from 0.01% to 15% by weight, more preferentially from 0.1% to 10% by weight, better still from 0.2% to 8% by weight, and even better still from 0.3% to 6% by weight relative to the total weight of the composition.

Advantageously, the total content of nonionic surfactant(s) in the composition preferably ranges from 0.05% to 15% by weight, more preferentially from 0.1% to 10% by weight, better still from 0.5% to 7% by weight, relative to the total weight of the composition.

The composition according to the present invention also comprises one or more alkaline agents and/or one or more dyes chosen from direct dyes, oxidation dyes and mixtures thereof, as defined below.

Alkaline Agent

The composition according to the present invention may also comprise one or more alkaline agents chosen from mineral, organic or hybrid alkaline agents.

Preferably, the composition according to the present invention comprises one or more mineral, organic or hybrid alkaline agents.

For the purposes of the present invention, the terms "alkaline agent" and "basifying agent" are used interchangeably.

The mineral basifying agent(s) are preferably chosen from aqueous ammonia, alkali metal carbonates or bicarbonates such as sodium (hydrogen) carbonate and potassium (hydrogen) carbonate, alkali metal or alkaline-earth metal phosphates such as sodium phosphates or potassium phosphates, sodium or potassium hydroxides, alkali metal or alkaline-earth metal silicates or metasilicates such as sodium metasilicate, and mixtures thereof.

The organic basifying agent(s) are preferably chosen from alkanolamines, amino acids, organic amines, oxyethylenated and/or oxypropylenated ethylenediamines, 1,3-diaminopropane, 1,3-diamino-2-propanol, spermine, spermidine and mixtures thereof.

The term "alkanolamine" means an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

In particular, the alkanolamine(s) are chosen from monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris (hydroxymethyl)aminomethane and mixtures thereof.

Advantageously, the amino acids are basic amino acids comprising an additional amine function. Such basic amino acids are preferably chosen from histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole. The organic amine may also be chosen from amino acid dipeptides. As amino acid dipeptides that may be used in the present invention, mention may notably be made of carnosine, anserine and balenine. The organic amine may also be chosen from compounds including a guanidine function. As amines of this type other than arginine that may be used in the present invention, mention may notably be made of creatine, creatinine, 1,1-dimethylguanidine, 1,1-diethylguanidine, glycocyamine, metformin, agmatine, n-amidoalanine, 3-guanidinopropionic acid, 4-guanidinobutyric acid and 2-([amino (imino)methyl]amino)ethane-1-sulfonic acid.

Use may be made in particular of guanidine carbonate or monoethanolamine hydrochloride as hybrid compounds.

The alkaline agent(s) that are useful according to the invention are preferably chosen from alkanolamines such as monoethanolamine, diethanolamine or triethanolamine; aqueous ammonia, carbonates or bicarbonates such as sodium (hydrogen) carbonate and potassium (hydrogen) carbonate, alkali metal or alkaline-earth metal silicates or metasilicates such as sodium metasilicate and mixtures thereof, more preferentially from aqueous ammonia and alkanolamines, better still from alkanolamines and even better still monoethanolamine.

Preferably, the basifying agents are organic.

In a particular embodiment, the composition according to the invention is free of aqueous ammonia.

Advantageously, when they are present, the total content of the alkaline agent(s) preferably ranges from 0.1% to 40% by weight.

In a preferred embodiment, the total content of the alkaline agent(s) is preferably greater than or equal to 5% by weight, preferentially ranging from 5% to 40% by weight, more preferentially from 6% to 30% by weight, even more preferentially from 8% to 20% by weight, better still from 10% to 15% by weight, relative to the total weight of the composition.

Advantageously, when they are present, the total content of the alkaline agent(s) preferably ranges from 0.1% to 40% by weight.

In a preferred embodiment, the total content of the alkaline agent(s) is preferably greater than or equal to 5% by weight, preferentially ranging from 5% to 40% by weight, more preferentially from 6% to 30% by weight, even more preferentially from 8% to 20% by weight, better still from 10% to 15% by weight, relative to the total weight of the composition.

In a particular embodiment, the total content of the alkaline agent(s) chosen from alkanolamines, preferably monoethanolamine, preferably ranges from 0.1% to 40% by weight, relative to the total weight of the composition.

In a preferred embodiment, the total content of the alkaline agent(s) chosen from the alkanolamines, preferably monoethanolamine, is preferably greater than or equal to 5% by weight, preferentially ranging from 5% to 40% by weight, more preferentially from 6% to 30% by weight, even more preferentially from 8% to 20% by weight, better still from 10% to 15% by weight, relative to the total weight of the composition.

According to one embodiment, the pH of the composition according to the invention is between 8 and 13; preferably between 9.0 and 12.

The pH of the composition may be adjusted to the desired value by means of acidic or alkaline agent(s) commonly used in the dyeing of keratin fibres, such as those described previously, or alternatively using buffer systems known to those skilled in the art.

The Dyes

The composition according to the present invention may comprise one or more dyes.

Preferably, the composition according to the present invention comprises one or more dyes chosen from oxidation dyes, direct dyes and mixtures thereof, more preferentially one or more dyes chosen from oxidation dyes.

The Dyes: Oxidation Dyes

The oxidation dyes may be chosen from one or more oxidation bases, optionally in combination with one or more couplers.

Preferably, the oxidation dye(s) comprise one or more oxidation bases.

Preferably, the composition according to the invention comprises one or more oxidation bases.

The oxidation bases may be present in the form of salts, solvates and/or solvates of salts.

The addition salts of the oxidation bases present in the composition according to the invention are notably chosen from the addition salts with an acid, such as the hydrochlorides, hydrobromides, sulfates, citrates, succinates, tartrates, lactates, tosylates, benzenesulfonates, methanesulfonates, phosphates and acetates, and the addition salts with a base such as sodium hydroxide, potassium hydroxide, aqueous ammonia, amines or alkanolamines.

Moreover, the solvates of the oxidation bases more particularly represent the hydrates of said oxidation bases and/or the combination of said oxidation bases with a linear or branched $C_1$ to $C_4$ alcohol such as methanol, ethanol, isopropanol or n-propanol. Preferably, the solvates are hydrates.

The oxidation bases may be chosen from para-phenylenediamines, bis(phenyl)alkylenediamines, para-aminophenols, ortho-aminophenols and heterocyclic bases, and the addition salts thereof, the solvates thereof, and solvates of the salts thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(3-hydroxyethyl)amino-2-chloroaniline, 2-β-hydroxyethyl-para-phenylenediamine, 2-methoxymethyl-para-phenylenediamine, 2-γ-hydroxypropyl-para-phenylenediamine; 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof, the solvates thereof, and solvates of the salts thereof.

Among the para-phenylenediamines mentioned above, para-phenylenediamine, para-tolylenediamine, 2-isopropyl-para-phenylenediamine, 2-β-hydroxyethyl-para-phenylenediamine, 2-methoxymethyl-para-phenylenediamine, 2-γ-hydroxypropyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(3-hydroxyethyl)-para-phenylenediamine, 2-chloro-para-phenylenediamine and 2-β-acetylaminoethyloxy-para-phenylenediamine, and the addition salts thereof, the solvates thereof, and solvates of the salts thereof are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof, the solvates thereof, and solvates of the salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof, the solvates thereof, and solvates of the salts thereof.

Among the ortho-aminophenols, examples that may be mentioned include 2-aminophenol, 2-amino-5-methylphenol, 2-amino-6-methylphenol and 5-acetamido-2-aminophenol, and the addition salts thereof, solvates thereof and solvates of the salts thereof.

Among the heterocyclic bases, examples that may be mentioned include pyridine derivatives, pyrimidine derivatives and pyrazole derivatives.

Among the pyridine derivatives, mention may be made of the compounds described, for example, in patents GB 1 026 978 and GB 1 153 196, such as 2,5-diaminopyridine, 2-(4-methoxyphenyl)amino-3-aminopyridine, 3,4-diaminopyridine, and the addition salts thereof, the solvates thereof, and solvates of the salts thereof.

Other pyridine oxidation bases that are useful in the present invention are the 3-aminopyrazolo[1,5-a]pyridine oxidation bases or their addition salts described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and 2-(3-amino-pyrazolo[1,5-a]pyridin-2-yl)oxyethanol, and the addition salts thereof, the solvates thereof, and solvates of the salts thereof.

Among the pyrimidine derivatives, mention may be made of the compounds described, for example, in patents DE 2359399, JP 88-169571, JP 05-63124 and EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)

amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof, the solvates thereof, and solvates of the salts thereof. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl)pyrazole and/or a salt thereof, solvates thereof, and solvates of the salts thereof.

Pyrazole derivatives that may also be mentioned include diamino-N,N-dihydropyrazolopyrazolones and notably those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one, the salts thereof, the solvates thereof, and solvates of the salts thereof.

Use will preferably be made of 2,3-diamino-6,7-dihydro-1H,5H-pyrazolo[1,2-a]pyrazol-1-one and/or a salt thereof, a solvate thereof, or a solvate of the salts thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or 2-(3-aminopyrazolo[1,5-a]pyridin-2-yl)oxyethanol and/or a salt thereof, a solvate thereof, and a solvate of the salts thereof.

Preferably, the oxidation base(s) are chosen from para-phenylenediamines, bis(phenyl)alkylenediamines, para-aminophenols, ortho-aminophenols, heterocyclic bases, and the corresponding addition salts, the solvates thereof and/or the solvates of the salts thereof, and mixtures thereof; more preferentially from 2-methoxymethyl-para-phenylenediamine, 2-β-hydroxyethyl-para-phenylenediamine, 2-γ-hydroxypropyl-para-phenylenediamine, and the addition salts thereof, the solvates thereof and/or the solvates of the salts thereof, and mixtures thereof.

In a particular embodiment, the composition according to the invention is free of oxidation bases chosen from para-phenylenediamine, para-toluenediamine, addition salts thereof, solvates thereof and solvates of the salts thereof.

The oxidation dye(s) may also comprise one or more couplers, which may be chosen from the couplers conventionally used for the dyeing of keratin fibres.

Preferably, the composition according to the invention comprises one or more couplers.

Preferably, the couplers are chosen from meta-phenylenediamines, meta-aminophenols, meta-diphenols, naphthalene-based couplers and heterocyclic couplers, and also the addition salts thereof, and/or the solvates thereof, and/or solvates of the salts thereof.

Examples that may be mentioned include 1,3-dihydroxybenzene, 1,3-dihydroxy-2-methylbenzene, 4-chloro-1,3-dihydroxybenzene, 1-hydroxy-3-aminobenzene, 1-methyl-2-hydroxy-4-β-hydroxyethylaminobenzene, 4-amino-2-hydroxytoluene, 5-amino-6-chloro-2-methylphenol, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 5-methoxy-6-hydroxyindole, 2-amino-3-hydroxypyridine, 6-hydroxybenzomorpholine, 2-amino-4-hydroxyethylaminoanisole, 3-amino-6-methoxy-2-methylaminopyridine, 3,5-diamino-2,6-dimethoxypyridine, 1-N-(β-hydroxyethyl)amino-3,4-methylenedioxybenzene, 2,6-bis(3-hydroxyethylamino)toluene, 6-hydroxyindoline, 2,6-dihydroxy-4-methylpyridine, 2-chloro-3,5-diaminopyridine, 2-chloro-3,5-diamino-6-methoxypyridine, 2-chloro-3,5-diamino-6-methylpyridine, 1-H-3-methylpyrazol-5-one, 1-phenyl-3-methylpyrazol-5-one, 4-(3,5-diaminopyridin-2-yl)-1-(2-hydroxyethyl)-1-methylpiperazin-1-ium chloride, 2,6-dimethylpyrazolo[1,5-b]-1,2,4-triazole, 2,4,6-trimethoxyaniline hydrochloride, 2,6-dimethyl[3,2-c]-1,2,4-triazole, 6-methylpyrazolo[1,5-a]benzimidazole and 2,6-diaminopyrazine, the addition salts thereof, and/or the solvates thereof, and/or solvates of the salts thereof, and mixtures thereof.

Preferably, the coupler(s) used in the invention are chosen from 1,3-dihydroxybenzene, 1,3-dihydroxy-2-methylbenzene, 4-chloro-1,3-dihydroxybenzene, 1-hydroxy-3-aminobenzene, 1-methyl-2-hydroxy-4-β-hydroxyethylaminobenzene, 4-amino-2-hydroxytoluene, 5-amino-6-chloro-2-methylphenol, 2,4-diamino-1-(β-hydroxyethyloxy)benzene, α-naphthol, 6-hydroxyindole, 2-amino-3-hydroxypyridine, 6-hydroxybenzomorpholine, 3-amino-6-methoxy-2-methylaminopyridine, 2-amino-4-hydroxyethylaminoanisole, hydroxyethyl-3,4-methylenedioxyaniline and 2-amino-5-ethylphenol, the addition salts thereof, and/or the solvates thereof, and/or solvates of the salts thereof, and mixtures thereof.

Even more preferentially, the coupler(s) used in the invention are chosen from 3-amino-6-methoxy-2-methylaminopyridine, 6-hydroxybenzomorpholine, 2,4-diamino-1-(β-hydroxyethyloxy)benzene, 2-amino-3-hydroxypyridine, 5-amino-6-chloro-2-methylphenol, 1-methyl-2-hydroxy-4-β-hydroxyethylaminobenzene, 2-amino-4-hydroxyethylaminoanisole, hydroxyethyl-3,4-methylenedioxyaniline, 2-amino-5-ethylphenol and 1-hydroxy-3-aminobenzene, the addition salts thereof, and/or the solvates thereof, and/or solvates of the salts thereof, and mixtures thereof.

In general, the addition salts of the couplers that may be used in the context of the invention are especially chosen from addition salts with an acid, such as hydrochlorides, hydrobromides, sulfates, citrates, succinates, tartrates, lactates, tosylates, benzenesulfonates, phosphates and acetates, and the addition salts with a base such as sodium hydroxide, potassium hydroxide, aqueous ammonia, amines or alkanolamines.

Moreover, the solvates more particularly represent the hydrates of these couplers and/or the combination of these couplers with a linear or branched $C_1$ to $C_4$ alcohol such as methanol, ethanol, isopropanol or n-propanol. Preferably, the solvates are hydrates.

Preferably, the oxidation dyes chosen from couplers are chosen from 6-hydroxybenzomorpholine, 2,4-diamino-1-(β-hydroxyethyloxy)benzene, 2-amino-3-hydroxypyridine, 5-amino-6-chloro-2-methylphenol, 1-methyl-2-hydroxy-4-β-hydroxyethylaminobenzene, 2-amino-4-hydroxyethyl-aminoanisole, hydroxyethyl-3,4-methylenedioxyaniline, 2-amino-5-ethylphenol, 1-hydroxy-3-aminobenzene, the addition salts thereof, the solvates thereof, and/or solvates of the salts thereof, and mixtures thereof.

Better still, the coupler(s) are chosen from: 6-hydroxy-benzomorpholine, the addition salts thereof, the solvates thereof and/or the solvates of the salts thereof, hydroxy-ethyl-3,4-methylenedioxyaniline, the addition salts thereof, the solvates thereof and/or the solvates of the salts thereof, 2-amino-5-ethylphenol, the addition salts thereof, the solvates thereof and/or the solvates of the salts thereof, and mixtures thereof.

In a particular embodiment, the composition according to the invention is free of oxidation couplers chosen from resorcinol, 2-methylresorcinol, 4-chlororesorcinol, the addition salts thereof, the solvates thereof and the solvates of the salts thereof.

Advantageously, when they are present, the oxidation dyes chosen from oxidation bases are present in a total content ranging from 0.0001% to 10% by weight, preferably from 0.005% to 7% by weight and more preferentially from 0.1% to 4% by weight, relative to the total weight of the composition.

Advantageously, when they are present, the oxidation dyes chosen from couplers are present in a total content ranging from 0.0001% to 10% by weight, preferably from 0.005% to 7% by weight and more preferentially from 0.1% to 4% by weight, relative to the total weight of the composition.

Advantageously, when they are present, the oxidation dyes are present in a total content ranging from 0.0001% to 10% by weight, preferably from 0.005% to 7% by weight, and more preferentially from 0.1% to 4% by weight, relative to the total weight of the composition.

The Dyes: The Direct Dyes

The term "direct dye" means natural and/or synthetic dyes, other than oxidation dyes. These are dyes that will spread superficially on the fibre.

The synthetic direct dyes are, for example, chosen from the dyes conventionally used for direct dyeing, and among which mention may be made of all the aromatic and/or non-aromatic dyes that are commonly used, such as nitrobenzene, azo, hydrazono, nitro(hetero)aryl, tri(hetero)arylmethane, (poly)methine, carbonyl, azine, porphyrin, metalloporphyrin, quinone and in particular anthraquinone, indoamine and phthalocyanine direct dyes, and mixtures thereof.

Among the nitrobenzene direct dyes, mention may be made of: 1,4-diamino-2-nitrobenzene, 1-amino-2-nitro-4-β-hydroxyethylaminobenzene, 1-amino-2-nitro-4-bis(β-hydroxyethyl)aminobenzene, 1,4-bis(β-hydroxyethylamino)-2-nitrobenzene, 1-β-hydroxyethylamino-2-nitro-4-bis(β-hydroxyethylamino)benzene, 1-β-hydroxyethylamino-2-nitro-4-aminobenzene, 1-β-hydroxyethylamino-2-nitro-4-(ethyl)(β-hydroxyethyl)aminobenzene, 1-amino-3-methyl-4-β-hydroxyethylamino-6-nitrobenzene, 1-amino-2-nitro-4-β-hydroxyethylamino-5-chlorobenzene, 1,2-diamino-4-nitrobenzene, 1-amino-2-β-hydroxyethylamino-5-nitrobenzene, 1,2-bis(3-hydroxyethylamino)-4-nitrobenzene, 1-amino-2-tris(hydroxymethyl)methylamino-5-nitrobenzene, 1-hydroxy-2-amino-5-nitrobenzene, 1-hydroxy-2-amino-4-nitrobenzene, 1-hydroxy-3-nitro-4-aminobenzene, 1-hydroxy-2-amino-4,6-dinitrobenzene, 1-β-hydroxyethyloxy-2-β-hydroxyethylamino-5-nitrobenzene, 1-methoxy-2-β-hydroxyethylamino-5-nitrobenzene, 1-β-hydroxyethyloxy-3-methylamino-4-nitrobenzene, 1-β,γ-dihydroxypropyloxy-3-methylamino-4-nitrobenzene, 1-β-hydroxyethylamino-4-β,γ-dihydroxypropyloxy-2-nitrobenzene, 1-0,7-dihydroxypropylamino-4-trifluoromethyl-2-nitrobenzene, 1-β-hydroxyethylamino-4-trifluoromethyl-2-nitrobenzene, 1-β-hydroxyethylamino-3-methyl-2-nitrobenzene, 1-β-aminoethylamino-5-methoxy-2-nitrobenzene, 1-hydroxy-2-chloro-6-ethylamino-4-nitrobenzene, 1-hydroxy-2-chloro-6-amino-4-nitrobenzene, 1-hydroxy-6-bis(3-hydroxyethyl)amino-3-nitrobenzene, 1-β-hydroxyethylamino-2-nitrobenzene, 1-hydroxy-4-β-hydroxyethylamino-3-nitrobenzene.

Among the azo direct dyes, mention may be made of: Basic Red 51, Basic Orange 31, Disperse Red 17, Acid Yellow 9, Acid Black 1, Basic Red 22, Basic Red 76, Basic Yellow 57, Acid Yellow 36, Acid Orange 7, Acid Red 33, Acid Red 35, Acid Yellow 23, Acid Orange 24, Disperse Black 9, Basic Brown 16, Basic Brown 17.

Among the hydrazono direct dyes, mention may be made of: Basic Yellow 87.

Among the nitroaryl direct dyes, mention may be made of: HC Blue 2, HC Yellow 2, HC Red 3,4-hydroxypropylamino-3-nitrophenol, N,N'-bis(2-hydroxyethyl)-2-nitrophenylenediamine.

Among the triarylmethane direct dyes, mention may be made of: Basic Violet 1, Basic Violet 2, Basic Violet 3, Basic Violet 4, Basic Violet 14, Basic Blue 1, Basic Blue 7, Basic Blue 26, Basic Green 1, Basic Blue 77 (also known as HC Blue 15), Acid Blue 1; Acid Blue 3; Acid Blue 7, Acid Blue 9; Acid Violet 49; Acid Green 3; Acid Green 5; Acid Green 50.

Among the quinone direct dyes, mention may be made of: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, 1,4-bis(0,7-dihydroxypropylamino)anthraquinone, Acid Blue 25, Acid Blue 43, Acid Blue 78, Acid Blue 129, Acid Blue 138, Acid Blue 140, Acid Blue 251, Acid Green 25, Acid Green 41, Acid Violet 42, Mordant Red 3, Acid Black 48, HC Blue 16.

Among the azine direct dyes, mention may be made of: Basic Blue 17, Basic Red 2.

Among the indoamine direct dyes, mention may be made of: 2-β-hydroxyethlyamino-5-[bis(β-4'-hydroxyethyl)amino]anilino-1,4-benzoquinone, 2-3-hydroxyethylamino-5-(2'-methoxy-4'-amino)anilino-1,4-benzoquinone, 3-N-(2'-chloro-4'-hydroxy)phenylacetylamino-6-methoxy-1,4-benzoquinoneimine, 3-N-(3'-chloro-4'-methylamino)phenylureido-6-methyl-1,4-benzoquinoneimine, 3-[4'-N-(ethylcarbamylmethyl)amino]phenylureido-6-methyl-1,4-benzoquinoneimine.

The natural direct dyes are chosen, for example, from lawsone, juglone, indigo, leuco indigo, indirubin, isatin, hennotannic acid, alizarin, carthamine, morin, purpurin, carminic acid, kermesic acid, laccaic acid, purpurogallin, protocatechaldehyde, curcumin, spinulosin, apigenidin, orceins, carotenoids, betanin, chlorophylls, chlorophyllines, monascus, polyphenols or ortho-diphenols.

Among the ortho-diphenols that are useful according to the invention, mention may be made of: catechin, quercetin, brazilin, haematein, haematoxylin, chlorogenic acid, caffeic acid, gallic acid, L-DOPA, cyanidin, (−)-epicatechin, (−)-epigallocatechin, (−)-epigallocatechin 3-gallate (EGCG), isoquercetin, pomiferin, esculetin, 6,7-dihydroxy-3-(3-hydroxy-2,4-dimethoxyphenyl)coumarin, santalin A and B, mangiferin, butein, maritimetin, sulfuretin, robtein, betanidin, pericampylinone A, theaflavin, proanthocyanidin A2, proanthocyanidin B2, proanthocyanidin C1, procyanidins DP 4-8, tannic acid, purpurogallin, 5,6-dihydroxy-2-methyl-1,4-naphthoquinone, alizarin, wedelolactone and natural extracts containing same.

When the composition comprises at least one direct dye, they are preferably present in a total content ranging from 0.001% to 20% by weight, preferably from 0.005% to 15% by weight, more preferentially from 0.01% to 10% by weight, better still from 0.05% to 5%, and even better still from 0.1% to 3% by weight, relative to the weight of the composition.

Preferably, the composition according to the invention comprises one or more dyes chosen from oxidation dyes and direct dyes, more preferentially chosen from oxidation dyes.

Preferably, the composition according to the invention comprises one or more alkaline agents and one or more dyes chosen from oxidation dyes, direct dyes, and mixtures thereof, in particular chosen from oxidation dyes.

Preferably, the composition according to the invention comprises:

- one or more compounds chosen from N,N-dicarboxymethylglutamic acid, salts thereof, solvates thereof, solvates of the salts thereof and mixtures thereof, in a content of greater than or equal to 3% by weight relative to the total weight of the composition,
- 1,3-propanediol,
- one or more nonionic surfactants, preferably chosen from ($C_6$-$C_{24}$ alkyl)polyglycosides, esters of $C_8$-$C_{30}$ fatty acids and of (poly)oxyalkylenated glycerol ethers, in particular of oxyethylenated and/or oxypropylenated glycerol ethers, and mixtures thereof,
- one or more alkaline agents and/or one or more dyes, preferably one or more organic alkaline agents and one or more dyes, in particular chosen from oxidation dyes.

Fatty Substance

The composition according to the invention may also comprise one or more fatty substances other than fatty acids.

The term "fatty substance" means an organic compound that is insoluble in water at 25° C. and at atmospheric pressure ($1.013\times10^5$ Pa) (solubility of less than 5% by weight, preferably less than 1% by weight and even more preferentially less than 0.1% by weight). They bear in their structure at least one hydrocarbon-based chain including at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

In other words, the term "fatty substances" means an organic compound that is insoluble in water at 25° C. and at atmospheric pressure ($1.013\times10^5$ Pa), in particular with a solubility of less than 5% by weight, preferably less than 1% by weight and even more preferentially less than 0.1% by weight.

The fatty substances are different from fatty acids.

In other words, the fatty substances are particularly different from fatty acids in free form, for instance fatty acids that are not in the form of esters (or fatty acids that are not esterified).

Preferably, the fatty substances do not comprise any carboxylic acid functions —COOH or any carboxylates functions $—COO^-$.

The fatty substances that may be used in the present invention are neither (poly)oxyalkylenated nor (poly)glycerolated.

In particular, the fatty substances are different from nonionic surfactants.

Preferably, the fatty substances according to the invention are neither (poly)oxyalkylenated or (poly)glycerolated and are different from nonionic surfactants.

Preferably, the fatty substances that are useful according to the invention are non-silicone fatty substances.

The term "non-silicone fatty substance" refers to a fatty substance not containing any Si—O bonds and the term "silicone fatty substance" refers to a fatty substance containing at least one Si—O bond.

Preferably, the fatty substances are non-silicone fatty substances different from nonionic surfactants and are in particular neither (poly)oxyalkylenated nor (poly)glycerolated.

The fatty substances that are useful according to the invention may be liquid fatty substances (or oils) and/or solid fatty substances. A liquid fatty substance is understood to be a fatty substance having a melting point of less than or equal to 25° C. at atmospheric pressure ($1.013\times10^5$ Pa). A solid fatty substance is understood to be a fatty substance having a melting point of greater than 25° C. at atmospheric pressure ($1.013\times10^5$ Pa).

For the purposes of the present invention, the melting point corresponds to the temperature of the most endothermic peak observed on thermal analysis (differential scanning calorimetry or DSC) as described in the standard ISO 11357-3; 1999. The melting point may be measured using a differential scanning calorimeter (DSC), for example the calorimeter sold under the name MDSC 2920 by the company TA Instruments. In the present patent application, all the melting points are determined at atmospheric pressure ($1.013\times10^5$ Pa).

More particularly, the liquid fatty substance(s) according to the invention may be chosen from $C_6$ to $C_{16}$ liquid hydrocarbons, liquid hydrocarbons comprising more than 16 carbon atoms, non-silicone oils of animal origin, oils of triglyceride type of plant or synthetic origin, fluoro oils, liquid fatty alcohols, liquid esters of fatty acid and/or of fatty alcohol other than triglycerides, and mixtures thereof.

It is recalled that the fatty alcohols and esters more particularly contain at least one saturated or unsaturated, linear or branched hydrocarbon-based group, comprising from 6 to 40 and better still from 8 to 30 carbon atoms, which is optionally substituted, in particular, with one or more hydroxyl groups (in particular 1 to 4). If they are unsaturated, these compounds may comprise one to three conjugated or unconjugated carbon-carbon double bonds.

As regards the $C_6$ to $C_{16}$ liquid hydrocarbons, these may be linear, branched, or optionally cyclic, and are preferably chosen from alkanes. Examples that may be mentioned include hexane, cyclohexane, undecane, dodecane, isododecane, tridecane or isoparaffins, such as isohexadecane or isodecane, and mixtures thereof.

The liquid hydrocarbons comprising more than 16 carbon atoms may be linear or branched, and of mineral or synthetic origin, and are preferably chosen from liquid paraffins or liquid petroleum jelly, polydecenes, hydrogenated polyisobutene such as Parleam®, and mixtures thereof.

A hydrocarbon-based oil of animal origin that may be mentioned is perhydrosqualene.

The triglyceride oils of plant or synthetic origin are preferably chosen from liquid fatty acid triglycerides including from 6 to 30 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, *macadamia* oil, arara oil, castor oil, avocado oil, caprylic/capric acid triglycerides, for instance those sold by the company Stdarinerie Dubois or those sold under the names Miglyol® 810, 812 and 818 by the company Dynamit Nobel, jojoba oil and shea butter oil, and mixtures thereof.

As regards the fluoro oils, they may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethylperfluoromorpholine sold under the name PF 5052® by the company 3M.

The liquid fatty alcohols that are suitable for use in the invention are more particularly chosen from linear or branched, saturated or unsaturated alcohols, preferably unsaturated or branched alcohols, including from 6 to 40 carbon atoms and preferably from 8 to 30 carbon atoms. These fatty alcohols are neither oxyalkylenated nor glycerolated. Examples that may be mentioned include octyldodecanol, 2-butyloctanol, 2-hexyldecanol, 2-undecylpentadecanol, isostearyl alcohol, oleyl alcohol, linolenyl alcohol, ricinoleyl alcohol, undecylenyl alcohol and linoleyl alcohol, and mixtures thereof. Preferably, oleyl alcohol will be used.

As regards the liquid esters of fatty acids and/or of fatty alcohols other than the triglycerides mentioned above, mention may be made notably of esters of saturated or unsaturated, linear $C_1$ to $C_{26}$ or branched $C_3$ to $C_{26}$ aliphatic monoacids or polyacids and of saturated or unsaturated, linear $C_1$ to $C_{26}$ or branched $C_3$ to $C_{26}$ aliphatic monoalcohols or polyalcohols, the total carbon number of the esters being greater than or equal to 6 and more advantageously greater than or equal to 10.

Preferably, for the esters of monoalcohols, at least one from among the alcohol and the acid is branched.

Among the monoesters, mention may be made of dihydroabietyl behenate; octyldodecyl behenate; isocetyl behenate; isostearyl lactate; lauryl lactate; linoleyl lactate; oleyl lactate; isostearyl octanoate; isocetyl octanoate; octyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; octyl isononanoate; 2-ethylhexyl isononanoate; octyldodecyl erucate; oleyl erucate; ethyl palmitate, isopropyl palmitate, 2-ethylhexyl palmitate, 2-octyldecyl palmitate, alkyl myristates such as isopropyl myristate, isobutyl stearate; 2-hexyldecyl laurate, and mixtures thereof.

Preferably, among the monoesters of monoacids and of monoalcohols, use will be made of ethyl palmitate and isopropyl palmitate, alkyl myristates such as isopropyl myristate or ethyl myristate, isocetyl stearate, 2-ethylhexyl isononanoate, isodecyl neopentanoate and isostearyl neopentanoate, and mixtures thereof.

Esters of $C_4$ to $C_{22}$ dicarboxylic or tricarboxylic acids and of $C_{12}$ to $C_{22}$ alcohols and esters of mono-, di- or tricarboxylic acids and of $C_2$ to $C_{26}$ di-, tri-, tetra- or pentahydroxy alcohols may also be used.

Mention may notably be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

The composition may also comprise, as fatty ester, sugar esters and diesters of $C_6$ to $C_{30}$, preferably $C_{12}$ to $C_{22}$, fatty acids. It is recalled that the term "sugar" refers to oxygen-bearing hydrocarbon-based compounds bearing several alcohol functions, with or without aldehyde or ketone functions, and which include at least 4 carbon atoms. These sugars may be monosaccharides, oligosaccharides or polysaccharides other than the anionic polysaccharides as described below.

Examples of suitable sugars that may be mentioned include sucrose, glucose, galactose, ribose, fucose, maltose, fructose, mannose, arabinose, xylose and lactose, and derivatives thereof, notably alkyl derivatives, such as methyl derivatives, for instance methylglucose.

The sugar esters of fatty acids may be chosen notably from the group comprising the esters or mixtures of esters of sugars described previously and of linear or branched, saturated or unsaturated $C_6$ to $C_{30}$ and preferably $C_{12}$ to $C_{22}$ fatty acids. If they are unsaturated, these compounds may comprise one to three conjugated or unconjugated carbon-carbon double bonds.

The esters may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates, arachidonates or mixtures thereof notably such as the mixed oleo-palmitate, oleo-stearate and palmito-stearate esters.

More particularly, use is made of monoesters and diesters and notably sucrose, glucose or methylglucose mono- or di-oleates, -stearates, -behenates, -oleopalmitates, -linoleates, -linolenates and -oleostearates, and mixtures thereof.

An example that may be mentioned is the product sold under the name Glucate® DO by the company Amerchol, which is a methylglucose dioleate.

Preferably, use will be made of a liquid ester of a monoacid and of a monoalcohol.

According to one embodiment, fatty substances that are useful according to the invention are chosen from liquid fatty substances, preferably from liquid hydrocarbons containing more than 16 carbon atoms, plant oils, liquid fatty alcohols and liquid fatty esters, and mixtures thereof, more preferentially from liquid fatty alcohols.

Preferentially, the liquid fatty substance(s) are chosen from liquid fatty alcohols, in particular oleyl alcohol.

The solid fatty substances preferably have a viscosity of greater than 2 Pa·s, measured at 25° C. and at a shear rate of 1 $s^{-1}$.

The solid fatty substance(s) are preferably chosen from solid fatty alcohols, solid esters of fatty acids and/or of fatty alcohols, waxes, ceramides and mixtures thereof.

The term "fatty alcohol" means a long-chain aliphatic alcohol comprising from 6 to 40 carbon atoms, preferably from 8 to 30 carbon atoms, and comprising at least one hydroxyl group OH. These fatty alcohols are neither oxy-alkylenated nor glycerolated.

The solid fatty alcohols may be saturated or unsaturated, and linear or branched, and include from 8 to 40 carbon atoms, preferably from 10 to 30 carbon atoms. Preferably, the solid fatty alcohols have the structure R—OH with R denoting a linear alkyl group, optionally substituted with one or more hydroxyl groups, comprising from 8 to 40, preferentially from 10 to 30 carbon atoms, or even from 12 to 24 atoms and even better still from 14 to 22 carbon atoms.

The solid fatty alcohols that may be used are preferably chosen from saturated or unsaturated, linear or branched, preferably linear and saturated, (mono)alcohols including from 8 to 40 carbon atoms, better still from 10 to 30, or even from 12 to 24 and even better still from 14 to 22 carbon atoms.

The solid fatty alcohols that may be used may be chosen, alone or as a mixture, from: myristyl alcohol (or 1-tetradecanol); cetyl alcohol (or 1-hexadecanol); stearyl alcohol (or 1-octadecanol); arachidyl alcohol (or 1-eicosanol); behenyl alcohol (or 1-docosanol); lignoceryl alcohol (or 1-tetracosanol); ceryl alcohol (or 1-hexacosanol); montanyl alcohol (or 1-octacosanol); myricyl alcohol (or 1-triacontanol).

Preferentially, the solid fatty alcohol is chosen from cetyl alcohol, stearyl alcohol, behenyl alcohol, myristyl alcohol, arachidyl alcohol, and mixtures thereof, such as cetylstearyl alcohol or cetearyl alcohol. Particularly preferably, the solid fatty alcohol is cetylstearyl alcohol or cetearyl alcohol.

The solid esters of a fatty acid and/or of a fatty alcohol that may be used are preferably chosen from esters derived from a $C_9$-$C_{26}$ carboxylic fatty acid and/or from a $C_9$-$C_{26}$ fatty alcohol.

Preferably, these solid fatty esters are esters of a linear or branched, saturated carboxylic acid including at least 10 carbon atoms, preferably from 10 to 30 carbon atoms and more particularly from 12 to 24 carbon atoms, and of a linear or branched, saturated monoalcohol, including at least 10 carbon atoms, preferably from 10 to 30 carbon atoms and more particularly from 12 to 24 carbon atoms. The saturated carboxylic acids may optionally be hydroxylated, and are preferably monocarboxylic acids.

Esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may notably be made of octyldodecyl behenate, isocetyl behenate, cetyl lactate, stearyl octanoate, octyl octanoate, cetyl octanoate, decyl oleate, hexyl stearate, octyl stearate, myristyl stearate, cetyl stearate, stearyl stearate, octyl pelargonate, cetyl myristate, myristyl myristate, stearyl myristate, diethyl sebacate, diisopropyl sebacate, diisopropyl adipate, di-n-propyl adipate, dioctyl adipate, dioctyl maleate, octyl palmitate, myristyl palmitate, cetyl palmitate, stearyl palmitate, and mixtures thereof.

Preferably, the solid esters of a fatty acid and/or of a fatty alcohol are chosen from $C_9$-$C_{26}$ alkyl palmitates, notably myristyl, cetyl or stearyl palmitate; $C_9$-$C_{26}$ alkyl myristates, such as cetyl myristate, stearyl myristate and myristyl myristate; and $C_9$-$C_{26}$alkyl stearates, notably myristyl stearate, cetyl stearate and stearyl stearate; and mixtures thereof.

For the purposes of the present invention, a wax is a lipophilic compound, which is solid at 25° C. and atmospheric pressure, with a reversible solid/liquid change of state, having a melting point greater than about 40° C., which may be up to 200° C., and having in the solid state anisotropic crystal organization. In general, the size of the wax crystals is such that the crystals diffract and/or scatter light, giving the composition that comprises them a more or less opaque cloudy appearance. By bringing the wax to its melting point, it is possible to make it miscible with oils and to form a microscopically homogeneous mixture, but on returning the temperature of the mixture to room temperature, recrystallization of the wax, which is microscopically and macroscopically detectable (opalescence), is obtained.

In particular, the waxes that are suitable for use in the invention may be chosen from waxes of animal, plant or mineral origin, non-silicone synthetic waxes, and mixtures thereof.

Mention may be made notably of hydrocarbon-based waxes, for instance beeswax, notably of organic origin, lanolin wax and Chinese insect waxes; rice bran wax, carnauba wax, candelilla wax, ouricury wax, esparto grass wax, berry wax, shellac wax, Japan wax and sumac wax; montan wax, orange wax and lemon wax, microcrystalline waxes, paraffins and ozokerite; polyethylene waxes, the waxes obtained by Fischer-Tropsch synthesis and waxy copolymers, and also esters thereof.

Mention may also be made of $C_{20}$ to $C_{60}$ microcrystalline waxes, such as Microwax HW.

Mention may also be made of the MW 500 polyethylene wax sold under the reference Permalen 50-L polyethylene.

Mention may also be made of waxes obtained by catalytic hydrogenation of animal or plant oils containing linear or branched $C_8$ to $C_{32}$ fatty chains. Among these waxes mention may notably be made of isomerized jojoba oil such as the trans-isomerized partially hydrogenated jojoba oil, notably the product manufactured or sold by the company Desert Whale under the commercial reference Iso-Jojoba-50®, hydrogenated sunflower oil, hydrogenated castor oil, hydrogenated coconut kernel oil, hydrogenated lanolin oil and bis(1,1,1-trimethylolpropane) tetrastearate, notably the product sold under the name Hest 2T-4S® by the company Heterene.

The waxes obtained by hydrogenation of castor oil esterified with cetyl alcohol, such as those sold under the names Phytowax Castor 16L64® and 22L73® by the company Sophim, may also be used.

A wax that may be also used is a $C_{20}$ to $C_{40}$ alkyl (hydroxystearyloxy)stearate (the alkyl group comprising from 20 to 40 carbon atoms), alone or as a mixture. Such a wax is notably sold under the names Kester Wax K 82 P®, Hydroxypolyester K 82 P® and Kester Wax K 80 P® by the company Koster Keunen.

It is also possible to use microwaxes in the compositions of the invention; mention may notably be made of carnauba microwaxes, such as the product sold under the name MicroCare 350® by the company Micro Powders, synthetic-wax microwaxes, such as the product sold under the name MicroEase 114S® by the company Micro Powders, microwaxes constituted of a mixture of carnauba wax and polyethylene wax, such as the products sold under the names Micro Care 300® and 310® by the company Micro Powders, microwaxes constituted of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, and polytetrafluoroethylene microwaxes, such as the products sold under the names Microslip 519® and 519 L® by the company Micro Powders.

The waxes are preferably chosen from mineral waxes, for instance paraffin, petroleum jelly, lignite or ozokerite wax; plant waxes, for instance cocoa butter or cork fibre or sugar cane waxes, olive tree wax, rice wax, hydrogenated jojoba wax, ouricury wax, carnauba wax, candelilla wax, esparto grass wax, or absolute waxes of flowers, such as the essential wax of blackcurrant blossom sold by the company Bertin (France); waxes of animal origin, for instance beeswaxes or modified beeswaxes (cera bellina), spermaceti, lanolin wax and lanolin derivatives; microcrystalline waxes; and mixtures thereof.

The ceramides, or ceramide analogues such as glycoceramides, which may be used in the compositions according to the invention, are known; mention may be made in particular of ceramides of classes I, II, III and V according to the Dawning classification.

The ceramides or analogues thereof that may be used preferably correspond to the following formula: $R^3CH(OH)CH(CH_2OR^2)(NHCOR^1)$, in which:

- $R^1$ denotes a linear or branched, saturated or unsaturated alkyl group, derived from $C_{14}$-$C_{30}$ fatty acids, it being possible for this group to be substituted with a hydroxyl group in the alpha position, or a hydroxyl group in the omega position esterified with a saturated or unsaturated $C_{16}$-$C_{30}$ fatty acid;
- $R^2$ denotes a hydrogen atom, a (glycosyl)n group, a (galactosyl)m group or a sulfogalactosyl group, in which n is an integer ranging from 1 to 4 and m is an integer ranging from 1 to 8;
- $R^3$ denotes a $C_{15}$-$C_{26}$ hydrocarbon-based group, saturated or unsaturated in the alpha position, this group possibly being substituted with one or more $C_1$-$C_{14}$ alkyl groups; it being understood that in the case of natural ceramides or glycoceramides, $R^3$ may also denote a $C_{15}$-$C_{26}$ alpha-hydroxyalkyl group, the hydroxyl group being optionally esterified with a $C_{16}$-$C_{30}$ alpha-hydroxy acid.

The ceramides that are more particularly preferred are the compounds for which $R^1$ denotes a saturated or unsaturated alkyl derived from $C_{16}$-$C_{22}$ fatty acids; $R^2$ denotes a hydrogen atom and $R^3$ denotes a saturated linear $C_{15}$ group.

Preferentially, use is made of ceramides for which $R^1$ denotes a saturated or unsaturated alkyl group derived from $C_{14}$-$C_{30}$ fatty acids; $R^2$ denotes a galactosyl or sulfogalactosyl group; and $R^3$ denotes a —CH═CH—$(CH_2)_{12}$—$CH_3$ group.

Use may also be made of the compounds for which $R^1$ denotes a saturated or unsaturated alkyl radical derived from $C_{12}$-$C_{22}$ fatty acids; $R^2$ denotes a galactosyl or sulfogalactosyl radical; and $R^3$ denotes a saturated or unsaturated $C_{12}$-$C_{22}$ hydrocarbon-based radical and preferably a —CH═CH—$(CH_2)_{12}$—$CH_3$ group.

As compounds that are particularly preferred, mention may also be made of 2-N-linoleoylaminooctadecane-1,3-diol; 2-N-oleoylaminooctadecane-1,3-diol; 2-N-palmitoylaminooctadecane-1,3-diol; 2-N-stearoylaminooctadecane-1,3-diol; 2-N-behenoylaminooctadecane-1,3-diol; 2-N-[2-hydroxypalmitoyl]aminooctadecane-1,3-diol; 2-N-stearoylaminooctadecane-1,3,4-triol and in particular N-stearoylphytosphingosine, 2-N-palmitoylaminohexadecane-1,3-diol, N-linoleoyldihydrosphingosine, N-oleoyldihydrosphingosine, N-palmitoyldihydrosphingosine, N-stearoyldihydrosphingosine, and N-behenoyldihydrosphingosine, N-docosanoyl-N-methyl-D-glucamine, cetylic acid N-(2-hydroxyethyl)-N-(3-cetyloxy-2-hydroxypropyl)amide and bis(N-hydroxyethyl-N-cetyl)malonamide; and mixtures thereof. N-Oleoyldihydrosphingosine will preferably be used.

The solid fatty substances are preferably chosen from the solid fatty alcohols and mixtures thereof.

According to a preferred embodiment, the composition according to the invention comprises one or more solid fatty substances, preferably chosen from solid fatty alcohols and mixtures thereof, in particular from cetyl alcohol, stearyl alcohol and mixtures thereof such as cetylstearyl alcohol or cetearyl alcohol.

Butters may also be used.

For the purposes of the present invention, the term "butter" (also referred to as a "pasty fatty substance") means a lipophilic fatty compound with a reversible solid/liquid change of state, including at a temperature of 25° C. and at atmospheric pressure (760 mmHg) a liquid fraction and a solid fraction. Preferably, the butter(s) according to the invention have a melting start temperature of more than 25° C. and a melting end temperature of less than 60° C.

Preferably, the particular butter(s) are of plant origin, such as those described in *Ullmann's Encyclopedia of Industrial Chemistry* ("Fats and Fatty Oils", A. Thomas, published online: Jun. 15, 2000, DOI: 10.1002/14356007.a10_173, point 13.2.2.2. Shea Butter, Borneo Tallow, and Related Fats (Vegetable Butters)).

Mention may be made more particularly of shea butter, Karité Nilotica butter (*Butyrospermum parkii*), galam butter, (*Butyrospermum parkii*), Borneo butter or fat or tengkawang tallow (*Shorea stenoptera*), *shorea* butter, illipé butter, *madhuca* butter or *Bassia madhuca longifolia* butter, mowrah butter (*Madhuca latifolia*), katiau butter (*Madhuca mottleyana*), phulwara butter (*M. butyracea*), mango butter (*Mangifera indica*), murumuru butter (*Astrocaryum murumuru*), kokum butter (*Garcinia indica*), ucuuba butter (*Virola sebifera*), tucuma butter, painya butter (Kpangnan) (*Pentadesma butyracea*), coffee butter (*Coffea arabica*), apricot butter (*Prunus armeniaca*), *macadamia* butter (*Macadamia ternifolia*), grapeseed butter (*Vitis vinifera*), avocado butter (*Persea gratissima*), olive butter (*Olea europaea*), sweet almond butter (*Prunus amygdalus dulcis*), cocoa butter and sunflower butter.

An example of a preferred butter is shea butter.

In a known manner, shea butter is extracted from the fruit (also called "kernels" or "nuts") of the *Butyrospemum parkii* tree. Each fruit contains between 45% and 55% fatty substance, which is generally extracted and refined.

According to another preferred embodiment, the composition according to the invention comprises one or more solid fatty substances other than fatty acids, preferably chosen from solid fatty alcohols and mixtures thereof, and one or more liquid fatty substances other than fatty acids, preferably chosen from liquid fatty alcohols and liquid fatty esters and mixtures thereof, more preferentially from liquid fatty alcohols.

Advantageously, the total content of the fatty substance(s) other than fatty acids is greater than or equal to 10% by weight, preferably ranging from 10% to 25% by weight, more preferentially from 12% to 20% by weight, even more preferentially from 14% to 18% by weight, relative to the total weight of the composition.

Advantageously, the total content of the solid fatty substance(s) other than fatty acids is greater than or equal to 10% by weight, preferably ranging from 10% to 25% by weight, more preferentially from 12% to 20% by weight, even more preferentially from 14% to 18% by weight, relative to the total weight of the composition.

Thickening Polymers

The composition according to the invention may comprise at least one thickening polymer, preferably chosen from polysaccharides, more preferentially from anionic polysaccharides.

Preferably, the composition according to the invention comprises one or more thickening polymer(s), preferably chosen from polysaccharides, more preferentially from anionic polysaccharides.

The term "polysaccharides" means polymers which contain at least 11 monosaccharide units. Preferentially, the polysaccharides of the invention include between 20 and 100 000 monosaccharide units.

The anionic polysaccharides according to the invention comprise one or more anionic or anionizable groups, and do not comprise any cationic or cationizable groups.

The anionic polysaccharides that are useful according to the invention may be chosen from those derived from the following sugars: glucose; galactose; arabinose; rhamnose; mannose; xylose; fucose; anhydrogalactose; galacturonic acid; glucuronic acid; mannuronic acid; galactose sulfate; anhydrogalactose sulfate.

The polymers bearing sugar units of the invention may be natural or synthetic.

According to a particular embodiment, the anionic polysaccharides that are useful according to the invention are chosen from native gums such as:

- tree or shrub exudates, for instance: acacia gum (branched polymer of galactose, arabinose, rhamnose and glucuronic acid); ghatti gum (polymer derived from arabinose, galactose, mannose, xylose and glucuronic acid); karaya gum (polymer derived from galacturonic acid, galactose, rhamnose and glucuronic acid); gum tragacanth (polymer of galacturonic acid, galactose, fucose, xylose and arabinose);
- gums derived from algae, such as: alginates (polymers of mannuronic acid and glucuronic acid); carrageenans and furcellerans (polymers of galactose sulfate and anhydrogalactose sulfate);
- microbial gums such as: xanthan gums (polymer of glucose, mannose acetate, mannose/pyruvic acid and glucuronic acid); gellan gums (polymer of partially acylated glucose, rhamnose and glucuronic acid).

For the purposes of the present invention, the term "microbial gums" means substances synthesized by fermentation of sugars by microorganisms.

According to a preferred embodiment, the anionic polysaccharides that are useful according to the invention are chosen from anionic gums, better still from anionic microbial gums, more preferentially from xanthan gums.

The total content of the thickening polymers as defined previously, when they are present in the composition according to the invention, preferably ranges from 0.01% to 10% by weight relative to the total weight of the composition, preferably from 0.05% to 8% by weight, better still from 0.1% to 5% by weight relative to the total weight of the composition.

The total content of anionic polysaccharides as defined previously, when they are present in the composition according to the invention, preferably ranges from 0.01% to 10% by weight relative to the total weight of the composition, preferably from 0.05% to 8% by weight, better still from 0.1% to 5% by weight relative to the total weight of the composition.

According to one embodiment, the total content of the anionic microbial gums as defined previously preferably ranges from 0.01% to 10% by weight relative to the total weight of the composition, preferably from 0.05% to 5% by weight, better still from 0.1% to 2% by weight relative to the total weight of the composition.

Anionic Surfactants

The composition according to the invention may also comprise one or more anionic surfactants.

Preferably, the composition according to the present invention comprises one or more anionic surfactants.

The term "anionic surfactant" means a surfactant including, as ionic or ionizable groups, only anionic groups. These anionic groups are preferably chosen from the following groups: $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2$, $PO_2^{2-}$, POH and $PO^-$.

As examples of anionic surfactants that can be used in the composition according to the invention, mention may be made of alkyl sulfates, alkyl ether sulfates, alkylamido ether sulfates, alkylaryl polyether sulfates, monoglyceride sulfates, alkyl sulfonates, alkylamide sulfonates, alkylaryl sulfonates, α-olefin sulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N—($C_1$-$C_4$)alkyl N-acyl taurates, salts of alkyl monoesters of polyglycoside-polycarboxylic acids, acyl lactylates, salts of D-galactoside uronic acids, salts of alkyl ether carboxylic acids, salts of alkylaryl ether carboxylic acids, salts of alkylamido ether carboxylic acids; fatty acid salts, and the corresponding non-salified forms of all these compounds; the alkyl and acyl groups of all these compounds (unless specified otherwise) generally including from 6 to 24 carbon atoms and the aryl group generally denoting a phenyl group.

These compounds may be oxyethylenated and then preferably include from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salt.

Examples of amino alcohol salts that may notably be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

The anionic surfactants that may be present may be mild anionic surfactants, i.e. anionic surfactants not bearing a sulfate function.

As regards the mild anionic surfactants, mention may be made in particular of the following compounds and salts thereof, and also mixtures thereof: polyoxyalkylenated alkyl ether carboxylic acids, polyoxyalkylenated alkylaryl ether carboxylic acids, polyoxyalkylenated alkylamido ether carboxylic acids, in particular those including 2 to 50 ethylene oxide groups, alkyl D-galactoside uronic acids, acyl sarcosinates, acyl glutamates and alkylpolyglycoside carboxylic esters.

Use may be made most particularly of polyoxyalkylenated alkyl ether carboxylic acids, for instance lauryl ether carboxylic acid (4.5 OE) sold, for example, under the name Akypo RLM 45 CA from Kao.

The anionic surfactants that may be present may be carboxylic acids comprising at least 8 carbon atoms, also known as fatty acids, optionally in salified form.

For the purposes of the present invention, the term “fatty acid” means an acid comprising at least one linear or branched, saturated or unsaturated hydrocarbon-based chain, such as an alkyl or alkenyl chain, including at least 6 carbon atoms, preferably from 8 to 24 carbon atoms, and better still from 10 to 22 carbon atoms.

The carboxylic acids comprising at least 6 carbon atoms (or fatty acids) according to the invention are neither (poly) oxyalkylenated, nor (poly)glycerolated; in particular, they are neither (poly)oxyethylenated, nor (poly)oxypropylenated.

They preferably have the structure R—COOH in which R denotes a linear or branched $C_7$-$C_{29}$, preferably $C_9$-$C_{23}$ and better still $C_9$-$C_{17}$ alkyl or alkenyl group.

Preferably, the fatty acid according to the invention is chosen from linear fatty acids, better still from unsaturated linear $C_{10}$-$C_{22}$ and notably $C_{10}$-$C_{18}$ fatty acids (R is a linear $C_9$-$C_{23}$ or even $C_9$-$C_{17}$ alkenyl).

Mention may notably be made of lauric acid, oleic acid, linoleic acid, linolenic acid, undecylenic acid, isocetylic acid, isostearic acid, cetylic acid, stearic acid and cetylstearylic acid, and mixtures thereof. Preferably, oleic acid will be used.

Among the anionic surfactants mentioned above, fatty acids are preferably used.

When the composition comprises one or more anionic surfactants, the total content of anionic surfactant(s) in the composition preferably ranges from 0.01% to 15% by weight, more preferentially from 0.1% to 10% by weight, better still from 0.5% to 8% by weight, even better still from 1% to 6% by weight, relative to the total weight of the composition.

When the composition comprises one or more anionic surfactants chosen from fatty acids, the total content of fatty acids in the composition preferably ranges from 0.01% to 15% by weight, more preferentially from 0.1% to 10% by weight, better still from 0.5% to 8% by weight, even better still from 1% to 6% by weight, relative to the total weight of the composition.

Solvents

The composition according to the invention may also comprise at least one organic solvent other than 1,3-propanediol.

Examples of organic solvents that may be mentioned include linear or branched $C_2$-$C_4$ alkanols, such as ethanol, propanol and isopropanol; polyols other than 1,3-propanediol and polyol ethers, for instance 2-butoxyethanol, propylene glycol, dipropylene glycol, glycerol, propylene glycol monomethyl ether, diethylene glycol monomethyl ether and monoethyl ether, and also aromatic alcohols or ethers, for instance benzyl alcohol or phenoxyethanol, and mixtures thereof.

Preferably, the organic solvent(s) are chosen from polyols; more preferentially, the organic solvent is glycerol.

The organic solvent(s) other than 1,3-propanediol may be present in a total amount ranging from 0.01% to 30% by weight, preferably ranging from 2% to 25% by weight, relative to the total weight of the composition.

In addition, the composition according to the invention is preferably an aqueous composition. The composition preferably comprises water in an amount of greater than or equal to 5% by weight, preferably greater than or equal to 10% by weight, and better still greater than or equal to 15% by weight, relative to the total weight of the composition.

Preferably, the water content ranges from 15% to 80% by weight, preferentially from 30% to 70% by weight and better still from 40% to 60% by weight.

Chemical Oxidizing Agents

The composition according to the invention may optionally also comprise one or more chemical oxidizing agents.

According to a particular embodiment, the composition according to the invention comprises one or more chemical oxidizing agents.

According to another particular embodiment, the composition according to the invention does not comprise any chemical oxidizing agents.

According to this embodiment, the composition according to the invention is preferably mixed at the time of use with at least one composition comprising one or more chemical oxidizing agents.

For the purposes of the present invention, the term “chemical oxidizing agent” means an oxidizing agent other than atmospheric oxygen.

The chemical oxidizing agent(s) (or decolourizing agents) that may be used in the present invention may be chosen from hydrogen peroxide, urea peroxide, alkali metal bromates, persalts such as perborates and persulfates, in particular sodium persulfate, potassium persulfate and ammonium persulfate, peracids and oxidase enzymes (with the optional cofactors thereof), among which mention may be made of peroxidases, 2-electron oxidoreductases such as uricases and 4-electron oxygenases such as laccases, and mixtures thereof; more preferentially, the chemical oxidizing agent(s) are chosen from hydrogen peroxide, persalts, and mixtures thereof, more preferably hydrogen peroxide.

Preferably, when they are present in the composition according to the invention, the chemical oxidizing agent(s) are present in a total content ranging from 0.1% to 35% by weight, more preferentially from 0.5% to 25% by weight and even more preferentially from 1% to 15% by weight, relative to the weight of the composition.

According to a preferred embodiment, when they are present in the composition according to the invention, the chemical oxidizing agent(s) chosen from hydrogen peroxide, persalts, and mixtures thereof are present in a total content ranging from 0.1% to 35% by weight, more preferentially from 0.5% to 25% by weight and even more preferentially from 1% to 15% by weight, relative to the weight of the composition.

Additives

The composition according to the invention may contain any commonly used adjuvant or additive other than the compounds described previously.

Among the additives that may be contained in the composition according to the invention, mention may be made of reducing agents, softeners, antifoams, moisturizers, UV-screening agents, peptizers, solubilizers, fragrances, anionic, cationic, amphoteric or zwitterionic surfactants, anionic polymers other than the anionic, cationic, nonionic and amphoteric polysaccharides or mixtures thereof, anti-dandruff agents, anti-seborrhoeic agents, vitamins and provitamins including panthenol, sunscreens, plasticizers, solubilizers, acidifying agents, mineral or organic thickeners, notably polymeric thickeners, antioxidants, hydroxy acids, fragrances, and preserving agents.

Needless to say, a person skilled in the art will take care to select this or these optional additional compounds such that the advantageous properties intrinsically associated with the composition according to the invention are not, or are not substantially, adversely affected by the envisaged addition(s).

The above additives may generally be present in an amount, for each of them, of between 0 and 20% by weight relative to the total weight of the composition.

Process

The present invention also relates to a process for dyeing and/or lightening keratin fibres, in particular human keratin fibres such as the hair, in which a composition is applied to said fibres, comprising:

- one or more compounds chosen from N,N-dicarboxymethylglutamic acid, salts thereof, solvates thereof, solvates of the salts thereof and mixtures thereof,
- 1,3-propanediol in a content of greater than or equal to 3% by weight relative to the total weight of the composition,
- one or more nonionic surfactants chosen from ($C_6$-$C_{24}$ alkyl)polyglycosides, esters of $C_8$-$C_{30}$ fatty acids and of (poly)oxyalkylenated glycerol ethers, in particular of oxyethylenated and/or oxypropylenated glycerol ethers, and mixtures thereof, as previously defined
- one or more dyes and/or one or more alkaline agents.

In particular, the present invention also relates to a process for dyeing keratin fibres, in particular human keratin fibres such as the hair, in which a composition is applied to said fibres, comprising:

- one or more compounds chosen from N,N-dicarboxymethylglutamic acid, salts thereof, solvates thereof, solvates of the salts thereof and mixtures thereof,
- 1,3-propanediol in a content of greater than or equal to 3% by weight relative to the total weight of the composition,
- one or more nonionic surfactants chosen from ($C_6$-$C_{24}$ alkyl)polyglycosides, esters of $C_8$-$C_{30}$ fatty acids and of (poly)oxyalkylenated glycerol ethers, in particular of oxyethylenated and/or oxypropylenated glycerol ethers, and mixtures thereof, as previously defined,
- one or more dyes,
- optionally one or more alkaline agents.

In other words, the dyeing process comprises at least the application of a composition according to the invention comprising one or more dyes. The dye(s) may be chosen from oxidation dyes, direct dyes and mixtures thereof, preferentially chosen from oxidation dyes.

Preferably, the composition according to the invention comprises one or more fatty substances as defined previously.

In particular, the dyeing process comprises at least one step of applying a composition as defined previously.

Preferably, the composition according to the invention is a composition for dyeing keratin fibres, such as the hair. Thus, preferably, the composition according to the invention comprises one or more dyes chosen from oxidation dyes, direct dyes and mixtures thereof as described previously, preferably from oxidation dyes.

Preferably, the dyeing process comprises at least the application to said keratin fibres of at least one composition according to the invention comprising one or more dyes chosen from oxidation dyes, direct dyes and mixtures thereof, preferably from oxidation dyes, in the presence of one or more chemical oxidizing agents, as defined previously, preferably hydrogen peroxide.

Preferably, the dyeing and/or lightening process comprises at least the application of a composition according to the invention comprising:

- one or more compounds chosen from N,N-dicarboxymethylglutamic acid, salts thereof, solvates thereof, solvates of the salts thereof and mixtures thereof,
- 1,3-propanediol in a content of greater than or equal to 3% by weight relative to the total weight of the composition,
- one or more nonionic surfactants chosen from ($C_6$-$C_{24}$ alkyl)polyglycosides, esters of $C_8$-$C_{30}$ fatty acids and of (poly)oxyalkylenated glycerol ethers, in particular of oxyethylenated and/or oxypropylenated glycerol ethers, and mixtures thereof, as previously defined,
- one or more dyes, as defined previously, and/or one or more alkaline agents, as defined previously,
- one or more oxidizing agents as defined previously, preferably hydrogen peroxide.

Preferably, the dyeing process comprises at least the application of a composition according to the invention comprising:

- one or more compounds chosen from N,N-dicarboxymethylglutamic acid, salts thereof, solvates thereof, solvates of the salts thereof and mixtures thereof,
- 1,3-propanediol in a content of greater than or equal to 3% by weight relative to the total weight of the composition,
- one or more nonionic surfactants chosen from ($C_6$-$C_{24}$ alkyl)polyglycosides, esters of $C_8$-$C_{30}$ fatty acids and of (poly)oxyalkylenated glycerol ethers, in particular of oxyethylenated and/or oxypropylenated glycerol ethers, and mixtures thereof, as previously defined,
- one or more dyes, as defined previously,
- optionally one or more alkaline agents, as defined previously,
- one or more chemical oxidizing agents as defined previously, preferably hydrogen peroxide.

According to a particular embodiment, the dyeing and/or lightening process comprises at least the use of a composition according to the invention and at least the use of a composition comprising one or more chemical oxidizing agents as defined previously, preferably hydrogen peroxide.

According to a particular embodiment, the dyeing and/or lightening process comprises at least the application to said fibres of a composition obtained by mixing, at the time of use:

- at least one composition, as defined above, comprising:
- one or more compounds chosen from N,N-dicarboxymethylglutamic acid, salts thereof, solvates thereof, solvates of the salts thereof and mixtures thereof,
- 1,3-propanediol in a content of greater than or equal to 3% by weight relative to the total weight of the composition,
- one or more nonionic surfactants chosen from ($C_6$-$C_{24}$ alkyl)polyglycosides, esters of $C_8$-$C_{30}$ fatty acids and of (poly)oxyalkylenated glycerol ethers, in particular of oxyethylenated and/or oxypropylenated glycerol ethers, and mixtures thereof, as previously defined,
- one or more dyes, as defined previously, and/or one or more alkaline agents, as defined previously,
- at least one composition comprising one or more chemical oxidizing agents as described previously, preferably hydrogen peroxide.

According to another particular embodiment, the dyeing process comprises at least the application to said fibres of a composition obtained by mixing at the time of use:

- at least one composition, as defined above, comprising:
- one or more compounds chosen from N,N-dicarboxymethylglutamic acid, salts thereof, solvates thereof, solvates of the salts thereof and mixtures thereof, 1,3-propanediol in a content of greater than or equal to 3% by weight relative to the total weight of the composition, one or more nonionic surfactants chosen from ($C_6$-$C_{24}$ alkyl)polyglycosides, esters of $C_8$-$C_{30}$ fatty acids and of (poly)oxyalkylenated glycerol ethers, in particular of oxyethylenated and/or oxypropylenated glycerol ethers, and mixtures thereof, as previously defined, one or more dyes, as defined previously, optionally one or more alkaline agents, as defined previously, at least one composition comprising one or more chemical oxidizing agents as described previously, preferably hydrogen peroxide.

The oxidizing composition is preferably an aqueous composition. In particular, it comprises more than 5% by weight of water, preferably more than 10% by weight of water and even more advantageously more than 20% by weight of water.

The oxidizing composition also preferably comprises one or more acidifying agents. Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

The oxidizing composition may also comprise fatty substances such as those described previously, preferably chosen from fatty alcohols, liquid hydrocarbons comprising more than 16 carbon atoms and mixtures thereof, surfactants and polymers.

Usually, the pH of the oxidizing composition, when it is aqueous, is less than 7.

Preferably, the oxidizing composition comprises hydrogen peroxide as oxidizing agent, in aqueous solution, the concentration of which ranges, more particularly, from 0.1% to 30% by weight, more particularly between 1% and 20% and even more preferentially between 2% and 15% by weight, relative to the weight of the oxidizing composition.

The present invention also relates to the use of the composition according to the invention as described previously for dyeing and/or lightening keratin fibres, in particular human keratin fibres such as the hair.

The composition according to the invention may be used on wet or dry keratin fibres, and also on any type of fair or dark, natural or dyed, permanent-waved, bleached or relaxed fibres.

According to a particular embodiment of the process of the invention, the fibres are washed before applying the composition described above.

The application of the composition of the invention to the keratin fibres may be performed via any conventional means, in particular by means of a comb, a fine brush, a coarse brush or with the fingers.

The colouring process, i.e. the application of the dye composition to the keratin fibres, is generally performed at room temperature (between 15 and 25° C.).

The composition according to the invention may be applied to the keratin fibres for a leave-on time ranging from 30 to 60 minutes.

After applying the composition according to the invention, the keratin fibres may optionally be washed with a shampoo and/or rinsed with water.

The present invention also relates to the use of the composition according to the invention as described previously for dyeing and/or lightening keratin fibres, preferably dyeing keratin fibres, in particular human keratin fibres such as the hair.

The present invention also relates to a ready-to-use composition, as defined above, comprising:

one or more compounds chosen from N,N-dicarboxymethylglutamic acid, solvates thereof, solvates of the salts thereof and mixtures thereof, 1,3-propanediol in a content of greater than or equal to 3% by weight relative to the total weight of the composition, one or more nonionic surfactants, as defined previously, preferably chosen from ($C_6$-$C_{24}$ alkyl)polyglycosides, and mixtures thereof, one or more dyes, as defined previously, and/or one or more alkaline agents, as defined previously, one or more chemical oxidizing agents as defined previously, preferably hydrogen peroxide.

The invention also relates to a multi-compartment device comprising at least a first compartment containing the composition according to the invention as described above and at least a second compartment containing one or more chemical oxidizing agents as described above, preferably hydrogen peroxide.

The examples that follow serve to illustrate the invention without, however, being limiting in nature.

EXAMPLES

Example 1

Compositions A1 and A2 (invention) and composition B1 (comparative) were prepared from the following ingredients, expressed as weight percentages:

TABLE 1

| | Composition B1 | Composition A1 | Composition A2 |
|---|---|---|---|
| Xanthan gum | 0.20 | 0.2 | 0.20 |
| Oleic acid | 2.7 | 2.7 | 2.7 |
| Ethanolamine | 12.2 | 12.2 | 12.2 |
| Cocoyl glucoside | 1.87 | 1.87 | 1.87 |
| Hydroxybenzomorpholine | 0.3 | 0.3 | 0.3 |
| 2-Methoxymethyl-p-phenylenediamine | 0.3 | 0.3 | 0.3 |
| 1,3-Propanediol | — | 3 | 5 |
| Tetrasodium glutamate diacetate | 0.24 | 0.24 | 0.24 |
| Glycerol | 5 | 5 | 5 |
| Cetearyl alcohol | 16.3 | 16.3 | 16.3 |
| Oleyl alcohol | 2.7 | 2.7 | 2.7 |
| Water | qs 100 | qs 100 | qs 100 |

Composition C was prepared from the ingredients below, expressed as weight percentages:

TABLE 2

| | Composition C |
|---|---|
| Trideceth-2 carboxamide MEA | 0.85 |
| Tetrasodium etidronate | 0.06 |
| Sodium salicylate | 0.035 |
| Glycerol | 0.50 |
| Cetearyl alcohol | 2.28 |
| Ceteareth-25 | 0.57 |
| Phosphoric acid | qs pH = 2.2 ± 0.2 |
| Hydrogen peroxide | 6 |
| Tetrasodium pyrophosphate | 0.04 |
| Water | qs 100 |

At the time of use, each of the compositions B1, A1 and A2 is mixed with 1.5 times its weight of composition C.

Each of the mixtures is then applied to a lock of moderately sensitized hair (alkaline solubility AS20), at a rate of 5 g of mixture per gram of hair.

After a leave-on time of 30 minutes on a plate thermostatically regulated at 27° C., the hair is rinsed, washed with a standard shampoo and dried.

Result—Chromaticity

The colouring of the hair is evaluated in the L*a*b* system, using a Konica Minolta CM-3600A spectrocolorimeter (illuminant D65, angle 10°, specular component included) in the CIELab system.

In this system, L* represents the lightness. The lower the value of L*, the darker and more powerful the colouring obtained. The chromaticity is measured by the values a* and b*, a* representing the red/green axis and b* the yellow/blue axis.

The chromaticity is given by the following formula:

$$C^*=(a^2+b^2)_{1/2}$$

The higher the value of C*, the better the chromaticity of the colour obtained.

The results are given in the table below:

TABLE 3

| | C* |
|---|---|
| Composition B1 | 25.6 |
| Composition A1 | 27.8 |
| Composition A2 | 27.6 |

Compositions A1 and A2 according to the invention respectively comprising 3% and 5% by weight of 1,3-propanediol lead to better chromaticity relative to the comparative composition B1 not comprising any 1,3-propanediol.

Example 2

Composition A3 (according to the invention) and composition B3 (comparative) were prepared from the following ingredients, expressed in % by weight:

TABLE 4

| | Composition A3 | Composition B3 |
|---|---|---|
| Xanthan gum | 0.27 | 0.27 |
| Oleic acid | 3.60 | 3.60 |
| Ethanolamine | 16.27 | 16.27 |

TABLE 4-continued

| | Composition A3 | Composition B3 |
|---|---|---|
| Coco glucoside | 2.5 | — |
| Glyceryl stearate | — | 2.5 |
| Hydroxybenzomorpholine | 0.90 | 0.90 |
| 2-methoxymethyl-p-phenylenediamine | 0.90 | 0.90 |
| 1,3-Propanediol | 6.67 | 6.67 |
| Tetrasodium glutamate diacetate | 0.32 | 0.32 |
| Glycerol | 6.67 | 6.67 |
| Cetearyl alcohol | 21.73 | 21.73 |
| Oleyl alcohol | 3.60 | 3.60 |
| Water | qs 100 | qs 100 |

Composition C3 was prepared from the following ingredients, expressed in % by weight: 0.04

TABLE 2

| | Composition C3 |
|---|---|
| Trideceth-2 carboxamide MEA | 0.85 |
| Tetrasodium etidronate | 0.06 |
| Sodium salicylate | 0.035 |
| Glycerol | 0.50 |
| Cetearyl alcohol | 2.28 |
| Ceteareth-25 | 0.57 |
| Phosphoric acid | qs pH = 2.2 ± 0.2 |
| Hydrogen peroxide | 6 |
| Tetrasodium pyrophosphate | 0.04 |
| Water | qs 100 |

At the moment of use, each of the compositions A3 and B3 is mixed with one and a half times of composition C3.

Each of the mixtures is then applied to a lock of permanent-waved hair containing 90% white hairs, in a proportion of 5 g of mixture per gram of hair.

After a leave-on time of 30 minutes on a plate thermostatically regulated at 27° C., the hair is rinsed, washed with a shampoo and dried.

The colouring of the hair is evaluated in the L*a*b* system, using a Konica Minolta CM-3600A spectrocolorimeter (illuminant D65, angle 10°, specular component included) in the CIELab system.

In this system, L* represents the lightness. The lower the value of L*, the darker and more powerful the colouring obtained.

The results are given in the table below:

TABLE 3

| | L* |
|---|---|
| Mixture A3 + C3 (invention) | 27.3 |
| Mixture B3 + C3 (comparative) | 29.4 |

The composition according to the invention comprising coco glucoside results in a better dyeing power compared to the comparative composition comprising glyceryl stearate.

Example 3

Composition A4 (according to the invention) and composition B4 (comparative) were prepared from the following ingredients, expressed in % of active material (AM):

TABLE 4

| | Composition A4 | Composition B4 |
|---|---|---|
| Xanthan gum | 0.2 | 0.2 |
| Oleic acid | 2.7 | 2.7 |
| Ethanolamine | 12.35 | 12.35 |
| 2-amino-3-hydroxypyridine | 0.01 | 0.01 |
| 6-hydroxyindole | 0.13 | 0.13 |
| Hydroxybenzomorpholine | 1.14 | 1.14 |
| 1,3-Propanediol | 5 | 5 |
| Ascorbic acid | 0.25 | 0.25 |
| Tetrasodium glutamate diacetate | 0.2 | — |
| EDTA | — | 0.2 |
| N,N-Bis(2-hydroxyethyl)-p-phenylenediamine sulfate | 0.16 | 0.16 |
| Cetearyl glucoside | 0.5 | 0.5 |
| Glycerin | 5 | 5 |
| m-Aminophenol | 0.38 | 0.38 |
| 2,4-diaminophenoxyethanol HCl | 0.05 | 0.05 |
| Cetearyl alcohol | 16.3 | 16.3 |
| Oleyl alcohol | 2.7 | 2.7 |
| Sodium metabisulfite | 0.71 | 0.71 |
| Hydroxyethyl-3,4-methylenedioxyaniline HCl | 0.23 | 0.23 |
| Toluene-2,5-diamine | 1.55 | 1.55 |
| Water | qs 100 | qs 100 |

Composition C4 was prepared from the following ingredients, expressed in % by weight:

TABLE 5

| | Composition C4 |
|---|---|
| Trideceth-2 carboxamide MEA | 0.85 |
| Tetrasodium etidronate | 0.06 |
| Sodium salicylate | 0.035 |
| Glycerol | 0.50 |
| Cetearyl alcohol | 2.28 |
| Ceteareth-25 | 0.57 |
| Phosphoric acid | qs pH = 2.2 ± 0.2 |
| Hydrogen peroxide | 6 |
| Tetrasodium pyrophosphate | 0.04 |
| Water | qs 100 |

At the moment of use, each of the compositions A4 and B4 is mixed with 1.5 times its weight of composition C4.

Each of the mixtures is then applied to locks of 90% white natural hair (WN) and permanent-waved hair (PW), in a proportion of 10 g of mixture per gram of hair.

After a leave-on time of 30 minutes on a plate thermostatically regulated at 27° C., the hair is rinsed, washed with a standard shampoo and dried.

Selectivity:

The colouring of the hair is evaluated in the L*a*b* system, using a Konica Minolta CM-3600A spectrocolorimeter (illuminant D65, angle 10°, specular component included) in the CIE Lab system.

The selectivity coloration ΔE corresponds to the variation in colour between the lock of colored natural white hair (WN), representative of the nature of the hair at the root, and the lock of colored permanent-waved hair (PW) which is representative of the nature of the hair at the tip.

The lower the value of ΔE, the lower the selectivity, and therefore the more uniform the coloration between the tip and the root of the hair.

The results are given in the table below:

TABLE 6

| | Lock type | L* | a* | b* | ΔE |
|---|---|---|---|---|---|
| Mixture A4 + | WN | 19.37 | 1.53 | 1.11 | 1.23 |
| C4 Invention | WP | 18.31 | 1.61 | 1.73 | |
| Mixture B4 + | WN | 22.5 | 1.6 | 2.23 | 3.71 |
| C4 Comparative | WP | 18.81 | 1.66 | 1.85 | |

The composition according to the invention, comprising GLDA, results in a better selectivity compared to the comparative composition comprising EDTA.

The invention claimed is:

1. A composition comprising:

one or more compounds comprising N,N-dicarboxymethylglutamic acid, salts thereof, solvates thereof, solvates of the salts thereof, or mixtures thereof, 1,3-propanediol in a content of greater than or equal to 3% by weight relative to a total weight of the composition, one or more nonionic surfactants comprising $C_6$-$C_{24}$ alkylpolyglycosides, esters of $C_8$-$C_{30}$ fatty acids, esters of polyoxyalkylenated glycerol ethers, esters of oxyalkylenated glycerol ethers, or mixtures thereof, and one or more alkaline agents and/or one or more dyes.

2. The composition according to claim 1, characterized in that the one or more compounds comprising N,N-dicarboxymethylglutamic acid, salts thereof, solvates thereof, solvates of the salts thereof, or mixtures thereof comprise alkali metal salts.

3. The composition according to claim 1, characterized in that a total content of the one or more compounds comprising N,N-dicarboxymethylglutamic acid, salts thereof, solvates thereof, solvates of the salts thereof, or mixtures thereof ranges from 0.001% to 15% by weight, relative to the total weight of the composition.

4. The composition according to claim 1, characterized in that the content of the 1,3-propanediol ranges from 3% to 15% by weight, relative to the total weight of the composition.

5. The composition according to claim 1, characterized in that it further comprises additional nonionic surfactants comprising:

oxyalkylenated $C_8$-$C_{24}$ alkylphenols;

saturated or unsaturated, linear or branched, oxyalkylenated or glycerolated $C_8$-$C_{40}$ alcohols;

saturated or unsaturated, linear or branched, oxyalkylenated $C_8$ to $C_{30}$ fatty acid amides;

esters of saturated or unsaturated, linear or branched, $C_8$-$C_{30}$ fatty acids and of polyethylene glycols;

oxyethylenated esters of saturated or unsaturated, linear or branched, $C_8$-$C_{30}$ fatty acids and of sorbitol;

fatty acid esters of sucrose;

$C_8$-$C_{30}$ alkenylpolyglucosides, $C_8$-$C_{30}$ alkenylglucosides, $C_8$-$C_{30}$ alkylpolyglucoside esters, or $C_8$-$C_{30}$ alkylglucoside esters, which are wherein the $C_8$-$C_{30}$ alkenylpolyglucosides and the $C_8$-$C_{30}$ alkenylglucosides are optionally oxyalkylenated comprising from 0 to 10 oxyalkylene units and comprising from 1 to 15 glucose units;

saturated or unsaturated oxyethylenated plant oils;

condensates of ethylene oxide and/or of propylene oxide;

N—$C_8$-$C_{30}$ alkylglucamine and N—$C_8$-$C_{30}$ acylmethylglucamine derivatives;

amine oxides, or mixtures thereof.

6. The composition according to claim 1, characterized in that a total content of the one or more nonionic surfactants ranges from 0.05% to 15% by weight, relative to the total weight of the composition.

7. The composition according to claim 1, characterized in that it comprises one or more alkaline agents.

8. The composition according to claim 1, characterized in that it comprises one or more dyes comprising oxidation dyes, direct dyes, or mixtures thereof.

9. The composition according to claim 1, characterized in that it further comprises one or more fatty substances other than fatty acids.

10. The composition according to claim 1, characterized in that it further comprises one or more chemical oxidizing agents.

11. A process for dyeing and/or lightening keratin fibres, comprising an application to said keratin fibres of a composition as defined in claim 1.

12. The process according to claim 11, characterized in that it comprises at least the application to said keratin fibres of a composition obtained by mixing, at a time of use:

at least one composition as defined in claim 1, and at least one composition comprising one or more chemical oxidizing agents.

13. A multi-compartment device comprising at least a first compartment containing a composition as defined according to claim 1 and at least a second compartment containing a composition comprising one or more chemical oxidizing agents.

14. The composition according to claim 1, characterized in that the esters of polyoxyalkylenated glycerol ethers comprise esters of polyoxyethylenated glycerol ethers, polyoxypropylenated glycerol ethers, or a combination thereof, and the esters of oxyalkylenated glycerol ethers comprise oxyethylenated glycerol ethers, oxypropylenated glycerol ethers, or a combination thereof.

15. The composition according to claim 1, characterized in that it further comprises one or more fatty substances other than fatty acids, wherein the one or more fatty substances comprise liquid fatty substances other than fatty acids, solid fatty substances other than fatty acids, or mixtures thereof.

* * * * *